US010893848B2

(12) United States Patent
Sato

(10) Patent No.: US 10,893,848 B2
(45) Date of Patent: Jan. 19, 2021

(54) ULTRASOUND DIAGNOSIS APPARATUS AND IMAGE PROCESSING APPARATUS

(71) Applicant: Toshiba Medical Systems Corporation, Otawara (JP)

(72) Inventor: Takeshi Sato, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 349 days.

(21) Appl. No.: 15/270,381

(22) Filed: Sep. 20, 2016

(65) Prior Publication Data

US 2017/0086793 A1    Mar. 30, 2017

(30) Foreign Application Priority Data

Sep. 29, 2015 (JP) .................................. 2015-192120

(51) Int. Cl.
*A61B 8/08* (2006.01)
*A61B 8/00* (2006.01)

(52) U.S. Cl.
CPC .......... *A61B 8/5207* (2013.01); *A61B 8/4416* (2013.01); *A61B 8/488* (2013.01); *A61B 8/5246* (2013.01); *A61B 8/5276* (2013.01)

(58) Field of Classification Search
CPC ..... A61B 8/5207; A61B 8/4416; A61B 8/488; A61B 8/5246; A61B 8/5276; G01S 15/8981; G01S 15/8977

(Continued)

(56) References Cited

U.S. PATENT DOCUMENTS 5,997,473 A * 12/1999 Taniguchi .............. A61B 5/062
                                              600/117
2009/0149759 A1 *  6/2009 Baba ........................ A61B 8/06
                                              600/454

(Continued)

FOREIGN PATENT DOCUMENTS

JP      2014-158698           9/2014
WO  WO-2014115782 A1 *  7/2014  ............... A61B 8/06

OTHER PUBLICATIONS

Bercoff et al, Ultrafast Compound Doppler Imaging: Providing Full Blood Flow Characterization, IEEE Trans Ultrason Ferroelectr Freq Control. Jan. 2011;58(1):134-47. doi: 10.1109/TUFFC.2011.1780. (Year: 2011).*

(Continued)

*Primary Examiner* — Amelie R Davis
*Assistant Examiner* — John Denny Li
(74) *Attorney, Agent, or Firm* — Oblon, McClelland, Maier & Neustadt, L.L.P.

(57) ABSTRACT

An ultrasound diagnosis apparatus includes filter coefficient acquiring circuitry configured to, based on a result of a principal component analysis using first data strings that are sets of data generated based on echo signals caused by transmission of ultrasound waves on the same scan line, obtain a filter coefficient that suppresses clutter components; deriving circuitry configured to use the filter coefficient to obtain, from target data strings contained in a region of interest among the first data strings, a second data string that is a set of data derived from echo signals based on a moving body present in the region of interest, and derive waveform information indicating temporal changes of the moving body by performing a frequency analysis on the second data string; and control circuitry configured to generate a wave- (Continued)

form information image based on the wave information and cause a monitor to display the waveform information image.

14 Claims, 15 Drawing Sheets

(58) Field of Classification Search
USPC .......................................................... 600/455
See application file for complete search history.

(56)     References Cited

U.S. PATENT DOCUMENTS

| | | | | |
|---|---|---|---|---|
| 2010/0280384 A1* | 11/2010 | Song | ...................... | A61B 8/488 |
| | | | | 600/453 |
| 2014/0316286 A1* | 10/2014 | Addison | .............. | A61B 5/7278 |
| | | | | 600/484 |
| 2015/0320395 A1* | 11/2015 | Sato | ........................ | A61B 8/06 |
| | | | | 600/455 |

OTHER PUBLICATIONS

Lok et al., Lossless Data Compression for Improving the Performance of a GPU-Based Beamformer, Ultrason Imaging. Apr. 2015; 37(2):135-51. doi: 10.1177/0161734614547280. Epub Aug. 18, 2014. (Year: 2014).*

Jeremy Bercoff, et al., "Ultrafast Compound Doppler Imaging: Providing Full Blood Flow Characterization", IEEE Transactions on Ultrasonics Ferroelectrics and Frequency Control, vol. 58, (1), 2011, 14 pgs.

* cited by examiner

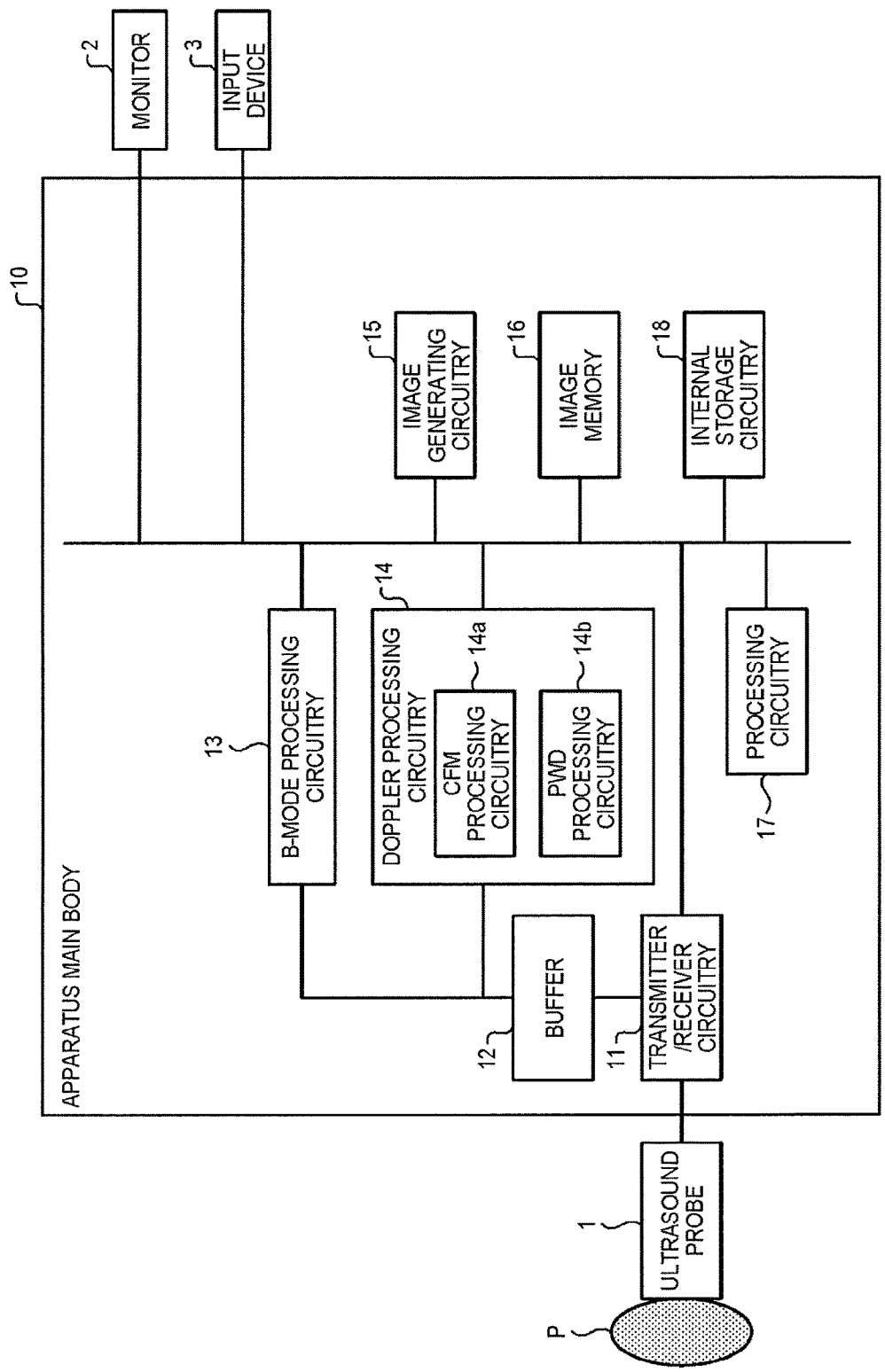

| | |
|---|---|
| $TH_1$ | 1000000dB |
| $TH_2$ | 1000000dB |
| $TH_3$ | 20dB |
| $TH_4$ | 15dB |
| $TH_5$ | 10dB |
| $TH_6$ | 5dB |
| $TH_7$ | -1dB |
| $TH_8$ | -1dB |

ULTRASOUND DIAGNOSIS APPARATUS AND IMAGE PROCESSING APPARATUS

CROSS-REFERENCE TO RELATED APPLICATIONS

This application is based upon and claims the benefit of priority from Japanese Patent Application No. 2015-192120, filed on Sep. 29, 2015; the entire contents of which are incorporated herein by reference.

FIELD

Embodiments described herein relate generally to an ultrasound diagnosis apparatus and an image processing apparatus.

BACKGROUND

The pulse wave Doppler (hereinafter, PWD) method is one method for displaying signals from a blood flow. In the PWD method, a Doppler waveform is generated by performing fast Fourier transform (FFT) on time-series data of signals received from the same location within a range defined by a range gate. In the PWD method, the power of a blood flow, expressed by use of luminance, is displayed with the horizontal axis representing time and the vertical axis representing frequencies.

In the PWD method, it is often the case that a high pass filter (HPF) of the infinite impulse response (IIR) type is applied to time-series data before FFT is performed thereon. In the case of performing FFT through fixed-point computation, the dynamic range of signals is insufficient when a signal near the direct-current component that has high signal intensity is included. For this reason, application of the HPF is necessary before FFT computation. By contrast, application of the HPF is not necessary when FFT is performed through floating-point computation. This HPF is also called a moving target indicator (MTI) filter or a wall filter.

BRIEF DESCRIPTION OF THE DRAWINGS

FIG. 1 is a diagram for explaining an exemplary configuration of an ultrasound diagnosis apparatus according to a first embodiment;

DETAILED DESCRIPTION

Figure 2A:
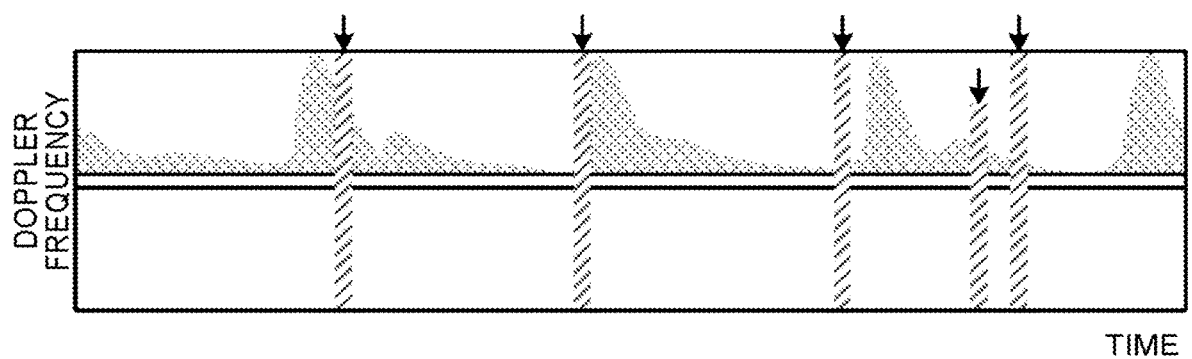
FIG. 2A is a diagram illustrating an example of an FFT display provided when, after a discontinuity has occurred in an input data string, FFT is performed with HPF processing of the IIR type performed prior thereto.

The following describes ultrasound diagnosis apparatuses and image processing apparatuses according to embodiments with reference to the drawings. However, embodiments are not limited to the embodiments described below. In addition, descriptions given for one embodiment are similarly applied to another embodiment as a general rule.

An ultrasound diagnosis apparatus according to one embodiment includes filter coefficient acquiring circuitry, deriving circuitry, and control circuitry. Based on a result of a principal component analysis using first data strings that are sets of data generated based on echo signals caused by transmission of ultrasound waves on the same scan line, the filter coefficient acquiring circuitry obtains a filter coefficient that suppresses clutter components. The deriving circuitry uses the filter coefficient to: obtain, from target data strings contained in a region of interest among the first data strings, a second data string that is a set of data derived from echo signals based on a moving body present in the region of interest; and derive waveform information indicating temporal changes of the moving body by performing a frequency analysis on the second data string. The control circuitry generates a waveform information image based on the wave information and causes a monitor to display the waveform information image.

First Embodiment

First, the following describes an exemplary configuration of an ultrasound diagnosis apparatus according to a first embodiment. FIG. 1 is a diagram for explaining an exemplary configuration of an ultrasound diagnosis apparatus according to the first embodiment. As illustrated in FIG. 1, the ultrasound diagnosis apparatus according to the first embodiment includes an ultrasound probe 1, a monitor 2, an input device 3, and an apparatus main body 10.

The ultrasound probe 1 includes a plurality of piezoelectric transducer elements. These piezoelectric transducer elements generate ultrasound waves based on drive signals supplied from transmitter/receiver circuitry 11 included in the apparatus main body 10 described later. The ultrasound probe 1 receives echo signals from a subject P and converts the received signals into electric signals. The ultrasound probe 1 also includes a matching layer and an acoustic lens that are provided to the piezoelectric transducer elements, a backing material for preventing ultrasound waves from being propagated backward from the piezoelectric transducer element, and the like. The ultrasound probe 1 is detachably connected to the apparatus main body 10.

When the ultrasound waves are transmitted from the ultrasound probe 1 to the subject P, the transmitted ultrasound waves are successively reflected by a surface across which the acoustic impedance is discontinuous in body tissue of the subject P, and received by the piezoelectric transducer elements included in the ultrasound probe 1 as echo signals. The amplitude of the echo signal received depends on a difference in the acoustic impedance on the discontinuous surface by which the corresponding ultrasound wave is reflected. When a transmitted ultrasound pulse is reflected by a surface of a moving blood flow, a cardiac wall, or the like, the corresponding echo signal is subjected to a frequency shift (Doppler shift) due to the Doppler effect depending on a velocity component of a moving body with respect to a direction in which ultrasound waves are transmitted.

The first embodiment is applicable to both of the following cases: where the subject P is two-dimensionally scanned by the ultrasound probe 1 that is a one-dimensional ultrasound probe having a plurality of piezoelectric transducer elements arranged in one line; and where the subject P is three-dimensionally scanned by the ultrasound probe 1 that mechanically swings a plurality of piezoelectric transducer elements in a one-dimensional ultrasound prove or by the ultrasound probe 1 that is a two-dimensional ultrasound probe having a plurality of piezoelectric transducer elements arranged two-dimensionally in a grid. Here, the one-dimensional ultrasound probe is capable of one-dimensionally scanning the subject P with one scan line. The two-dimensional ultrasound probe is capable of two-dimensionally scanning the subject P by focusing and transmitting ultrasound waves.

The ultrasound diagnosis apparatus according to the first embodiment is capable of imaging color Doppler images as described later. The ultrasound diagnosis apparatus according to the first embodiment is also capable of acquiring Doppler waveforms in a sample volume set on a B-mode image, a color Doppler image, or an image obtained by superimposing a color Doppler image on a part of a B-mode image, as described later. For these capabilities, the ultrasound probe 1 may be switched from one type to another in accordance with the kind of images to be acquired, for example, from the ultrasound probe 1 of a kind intended for use in performing the color flow mapping (CFM) method, to the ultrasound probe 1 of another kind intended for use in performing the continuous wave (CW) Doppler method or the pulsed wave (PW) Doppler method. The sample volume above may be called a range gate in some cases. A sample volume and a range gate are examples of a region of interest.

The input device 3 includes a mouse, a keyboard, a button, a panel switch, a touch command screen, a foot switch, a track ball, and the like, and receives various setting requests from an operator of the ultrasound diagnosis apparatus, and transfers the received various setting requests to the apparatus main body 10.

For example, the input device 3 receives, from an operator, setting as a region of interest (ROI) that is used by image generating circuitry 15 described later for performing image processing, and setting of a sample volume as an ROI that is used by PWD processing circuitry 14b described later for performing processing. An ROI that the input device 3 receives in the first embodiment is described later in detail.

The monitor 2 displays a graphical user interface (GUI) through which the operator of the ultrasound diagnosis apparatus inputs various setting requests using the input device 3, and displays ultrasound images generated in the apparatus main body 10 and other data.

The apparatus main body 10 is an apparatus that generates ultrasound images based on echo signals received by the ultrasound probe 1. The apparatus main body 10 includes, as illustrated in FIG. 1, the transmitter/receiver circuitry 11, a buffer 12, B-mode processing circuitry 13, Doppler processing circuitry 14, the image generating circuitry 15, an image memory 16, processing circuitry 17, and internal storage circuitry 18.

The transmitter/receiver circuitry 11 includes trigger generating circuitry, transmission delay circuitry, pulser circuitry, and the like, and supplies drive signals to the ultrasound probe 1. The pulser circuitry repeatedly generates, at a predetermined pulse repetition frequency (PRF), rate pulses for forming ultrasound waves to be transmitted. A PRF is also called a rate frequency. The transmission delay circuitry gives transmission delay times for the respective piezoelectric transducer elements to corresponding rate pulses generated by the pulser circuitry. The transmission delay times are needed for determining the transmission directivity by focusing ultrasound waves generated from the ultrasound probe 1 into a beam. The trigger generating circuitry applies drive signals (drive pulses) to the ultrasound probe 1 at timings based on the rate pulse. That is, the transmission delay circuitry changes the transmission delay time to be given to each rate pulse, thereby adjusting as desired the direction in which ultrasound waves are transmitted from the surface of the piezoelectric transducer elements.

The transmitter/receiver circuitry 11 has a function for immediately changing a transmission frequency, a transmission driving voltage, and the like to execute a predetermined scanning sequence based on instructions from the processing circuitry 17 described later. Specifically, the transmission driving voltage can be changed with linear amplifier type oscillator circuitry that can immediately switch the value thereof, or a mechanism that electrically switches a plurality of power supply units.

The transmitter/receiver circuitry 11 includes amplifier circuitry, an analog/digital (A/D) converter, reception delay circuitry, an adder, quadrature detection circuitry, and the like, and generates echo data by performing various types of processing on echo signals received by the ultrasound probe 1. The amplifier circuitry amplifies echo signals for each channel, and performs gain correction processing on the amplified echo signals. The A/D converter A/D converts the gain-corrected echo signals. The reception delay circuitry gives reception delay times needed for determining the reception directivity to digital data. The adder performs addition processing on the echo signals subjected to the processing by the reception delay circuitry. As a result of the addition processing by the adder, a reflection component from a direction corresponding to the reception directivity of the echo signal is enhanced. The quadrature detection circuitry converts an output signal from the adder into an in-phase signal (I signal where I is "in-phase") and a quadrature-phase signal (Q signal where Q is "quadrature-phase") in a baseband. The quadrature detection circuitry then stores, as the echo data, the I signal and the Q signal (hereinafter, referred to as I/Q signals) in the buffer 12 in the subsequent stage. The transmitter/receiver circuitry 11 thus controls the transmission directivity and the reception directivity in transmission and reception of ultrasound waves.

The buffer 12 is a buffer that temporarily stores therein the echo data (I/Q signals) generated by the transmitter/receiver circuitry 11. Specifically, the buffer 12 retains I/Q signals the data volume of which corresponds to the storage capacity thereof. For example, the buffer 12 is a first-in/first-out (FIFO) memory, and stores therein I/Q signals for a certain number of frames. When I/Q signals for one frame are newly generated by the transmitter/receiver circuitry 11, the buffer 12 discards I/Q signals for one frame generated at the oldest time, and stores therein the I/Q signals for one frame newly generated.

I/Q signals for one frame mean, for example, echo data for generating one ultrasound image, and the transmitter/receiver circuitry 11 generates I/Q signals for one frame by causing the ultrasound probe 1 to transmit and receive ultrasound waves within a scanning range formed of a plurality of scan lines.

The B-mode processing circuitry 13 reads out echo data (I/Q signals) generated by the transmitter/receiver circuitry 11 from the buffer 12, and performs processing such as logarithmic amplification, envelope detection processing, and logarithmic compression on the echo data thus read out, thereby generating data (B-mode data) in which signal intensity is represented by brightness of luminance.

The Doppler processing circuitry 14 reads out echo data (I/Q signals) generated by the transmitter/receiver circuitry 11 from the buffer 12, and performs frequency analysis on the echo data thus read out, thereby extracting a Doppler shift (Doppler shift frequency). By using the Doppler shift, the Doppler processing circuitry 14 extracts a blood flow, tissue, and an echo component from a contrast agent that are based on the Doppler effect, and generates data (Doppler data) obtained by extracting moving body information such as average velocity, dispersion, and power with respect to each of multiple points or one point.

Specifically, as illustrated in FIG. 1, the Doppler processing circuitry 14 includes CFM processing circuitry 14*a* and the PWD processing circuitry 14*b*. The CFM processing circuitry 14*a* is a processing unit that generates, by the CFM method, Doppler data for use in generating a color Doppler image. The CFM processing circuitry 14*a* acquires moving body information (blood flow information) on a blood flow within a scanning range by the autocorrelation method.

The PWD processing circuitry 14*b* is a processing unit that generates, by the PWD method, Doppler data for use in generating a Doppler waveform. The PWD processing circuitry 14*b* performs frequency analysis, thereby acquiring waveform information indicating temporal changes of a blood flow found in a sample volume. For example, the PWD processing circuitry 14*b* performs frequency analysis based on the fast Fourier transform (FFT) method, thereby acquiring waveform information indicating temporal changes of a blood flow found in a sample volume. Frequency analysis that the PWD processing circuitry 14*b* performs may be based on a method other than the FFT method insofar as Doppler data from which a Doppler waveform can be generated can be acquired by this other method. Processing that the PWD processing circuitry 14*b* performs is described later. Optionally, the Doppler processing circuitry 14 may include a processing unit for performing the tissue Doppler method.

The image generating circuitry 15 generates image data for display by using data generated by the B-mode processing circuitry 13 and the Doppler processing circuitry 14. That is, the image generating circuitry 15 generates, from B-mode data generated by the B-mode processing circuitry 13, a B-mode image in which the intensity of each echo signal is represented by luminance. The image generating circuitry 15 also generates a color Doppler image from Doppler data generated by the CFM processing circuitry 14*a*. The color Doppler image is any one of the following images: a velocity image, a dispersion image, and a power image that represent moving body information (blood flow information) on a blood flow; and an image obtained by combining two or more of these images. For example, the image generating circuitry 15 generates a power image in which different reddish color tones represent differences in power values. The image generating circuitry 15 is capable of also generating a power image other than a color Doppler image to be displayed in color, for example, a grayscale power image in which different grayscale levels of luminance represent different power values.

An image such as a color Doppler image that is generated by the image generating circuitry 15 from data generated by the CFM processing circuitry 14*a* is referred to as a "blood flow image" hereinafter.

The image generating circuitry 15 further generates, from Doppler data generated by the PWD processing circuitry 14*b*, a Doppler waveform obtained by plotting velocity information on the blood flow in a time series. In other words, the image generating circuitry 15 generates a Doppler waveform based on the waveform information. Specifically, the image generating circuitry 15 generates a time course curve with the vertical axis representing the velocity of the blood flow within the sample volume and the horizontal axis representing time. The image generating circuitry 15 then generates the Doppler waveform by setting the width in the vertical axis direction in accordance with dispersion values of the blood flow within the sample volume and setting values of the luminance in accordance with power values of the blood flow within the sample volume. A Doppler waveform is also referred to as a waveform information image.

Here, the image generating circuitry 15 typically converts (scan-converts) a scan line signal string of ultrasound scanning into a scan line signal string of a video format represented by a television, and generates an ultrasound image (B-mode image or blood flow image) as an image to be displayed. Specifically, the image generating circuitry 15 performs coordinate transformation according to a mode in which the ultrasound probe 1 performs ultrasound scanning, thereby generating an ultrasound image as an image to be displayed. In addition to the scan-converting, the image generating circuitry 15 performs, as various types of image processing, image processing (smoothing processing) for regenerating a luminance-value averaged image using a plurality of scan-converted image frames, or image processing (edge reinforcement processing) using a differential filter within the image, for example.

When transmission and reception of ultrasound waves are two-dimensionally performed, the image generating circuitry 15 performs coordinate transformation, thereby generating a two-dimensional B-mode image or a two-dimensional blood flow image as an image to be displayed. When transmission and reception of ultrasound waves are three-dimensionally performed, the image generating circuitry 15 generates volume data (a three-dimensional B-mode image or a three-dimensional blood flow image) and then generates, from the volume data, a two-dimensional image to be displayed on the monitor 2 by various types of rendering processing.

The image generating circuitry 15 generates a synthetic image in which character information of various parameters, a scale, a body mark, and the like are synthesized with various images. In addition, the image generating circuitry 15 generates a superimposition image having various images superimposed one another, such as a superimposition image with a B-mode image and a color Doppler image, and generates an image for displaying various images side by side.

The image memory 16 is a memory that stores therein various types of data generated by the image generating circuitry 15. The image memory 16 can store therein data (raw data) generated by the B-mode processing circuitry 13 and the Doppler processing circuitry 14. The image memory 16 can store therein data retained in the buffer 12 as needed.

The internal storage circuitry 18 stores therein various types of data such as control programs for performing transmission and reception of ultrasound waves, image processing, and display processing, diagnostic information (for example, patient identification data (ID) and findings of a doctor), a diagnostic protocol, and various body marks. The internal storage circuitry 18 is also used, for example, for archiving data stored in the image memory 16 as needed. The data stored in the internal storage circuitry 18 can be transferred to an external peripheral device via an interface (not illustrated).

The processing circuitry 17 controls the entire processing in the ultrasound diagnosis apparatus. Specifically, the processing circuitry 17 controls processing that the transmitter/receiver circuitry 11, the B-mode processing circuitry 13, the Doppler processing circuitry 14, and the image generating circuitry 15 perform, based on various setting requests input by the operator through the input device 3 and various control programs and various types of data read from the internal storage circuitry 18. The processing circuitry 17 performs control so that data stored in the image memory 16 and a GUI and the like to be used by the operator for designating the various types of processing can be displayed on the monitor 2. Displaying a Doppler waveform using the PWD method or the DWD method is referred to also as "FFT display". Displaying a blood flow image (color Doppler image) using the CFM method is referred to also as color Doppler display hereinafter.

The entire configuration of the ultrasound diagnosis apparatus according to the first embodiment is described above. With this configuration, the ultrasound diagnosis apparatus according to the first embodiment generates a Doppler waveform by the PWD method. In the PWD method, when a vascular wall or a valve of a heart is contained in a range gate, noise attributable to clutter may be mixed into a Doppler waveform. This is because a discontinuity occurs in an input data string as a result of appearance of an echo source that has not been present up to the present time or disappearance of an echo source that has been present up to the present time. Such appearance and disappearance are caused by an instantaneous movement of the vascular wall or the valve of a heart or by a change in specular reflection condition.

Figure 2B:
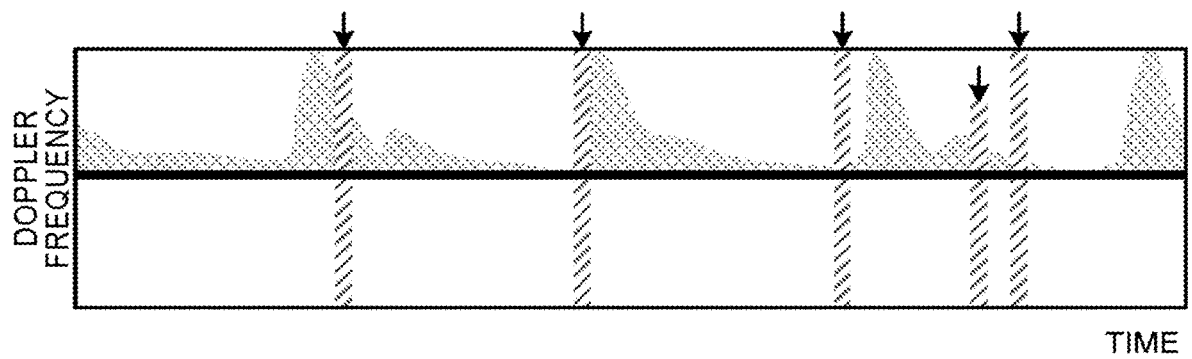
FIG. 2B is a diagram illustrating an example of an FFT display provided when, after a discontinuity has occurred in an input data string, FFT is performed without HPF processing performed prior thereto.

FIG. 2A is a diagram illustrating an example of an FFT display provided when, after a discontinuity has occurred in an input data string, FFT is performed with HPF processing of the IIR type performed prior thereto; and FIG. 2B is a diagram illustrating an example of an FFT display provided when, after a discontinuity has occurred in an input data string, FFT is performed without HPF processing performed prior thereto. In each of FIG. 2A and FIG. 2B, the horizontal axis represents time and the vertical axis represents Doppler frequencies. In FIG. 2A and FIG. 2B, luminance represents power.

As illustrated in FIG. 2A, after a discontinuity has occurred in an input data string, even when FFT is performed with HPF processing performed prior thereto, noise attributable to clutter is mixed into a Doppler waveform over a wide Doppler frequency range. In FIG. 2A, noise is indicated by arrows. That is, the occurrence of a discontinuity in an input data string makes it impossible to eliminate clutter noise mixed into a high Doppler frequency range that contains blood flow signals. As illustrated in FIG. 2B, when FFT is performed without HPF processing performed prior thereto, noise attributable to clutter is similarly mixed into a Doppler waveform over a wide Doppler frequency range. In FIG. 2B, noise is indicated by arrows. In addition, as illustrated in FIG. 2B, when FFT is performed without HPF processing performed prior thereto, a streak appears in the central portion because levels of frequency resolution are different between frequencies that are integer multiples of the number of FFT points and frequencies that are not integer multiples of the number of FFT points. As illustrated in FIG. 2A and FIG. 2B, the occurrence of a discontinuity in an input data string makes it impossible to eliminate clutter noise mixed into a high Doppler frequency range that contains blood flow signals.

Figure 3:
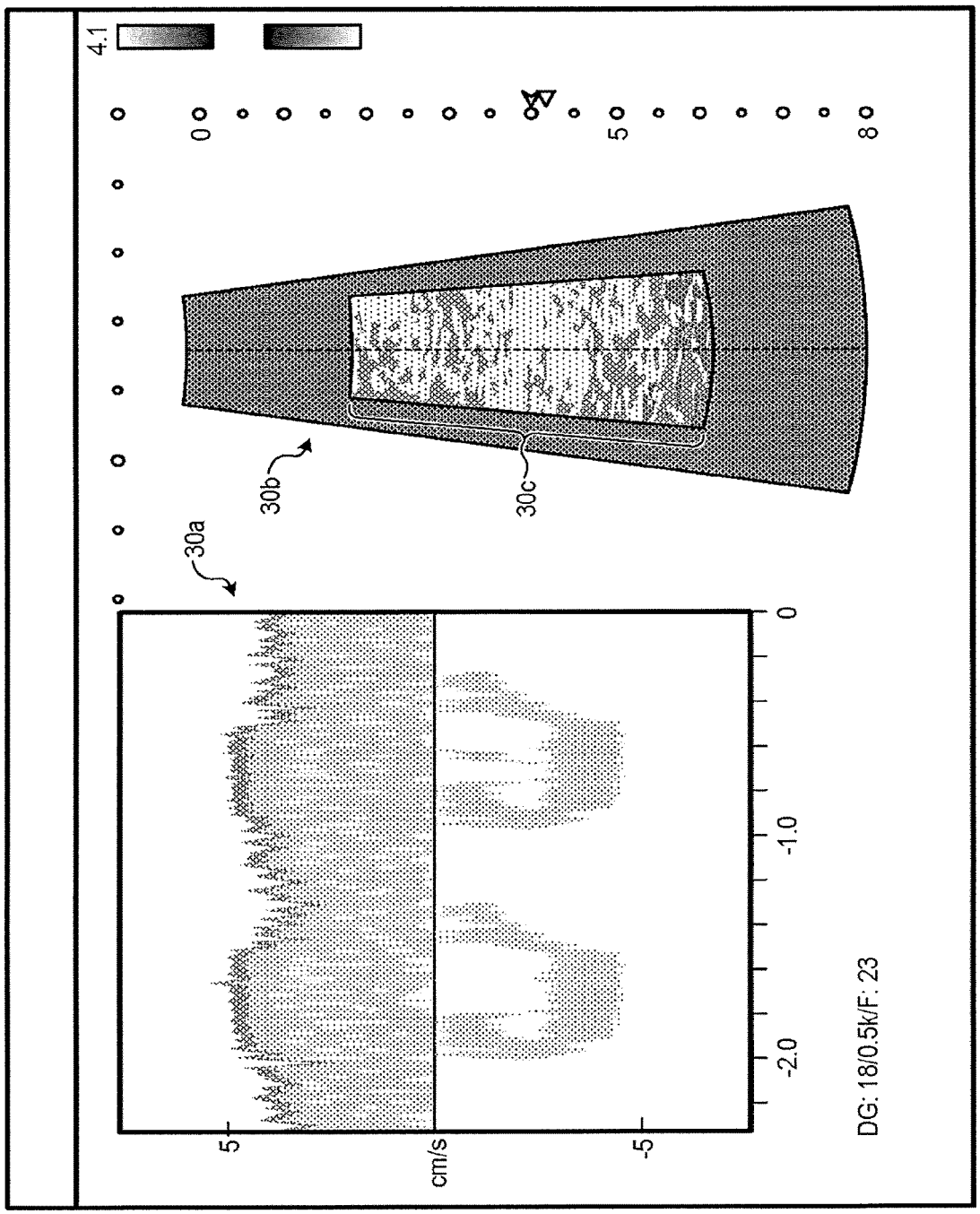
FIG. 3 is a diagram illustrating an example of an FFT display provided when the Doppler frequency of clutter overlaps the Doppler frequency of a blood flow.

In addition, even when no discontinuity has occurred in an input data string such as the one described above, noise attributable to clutter is mixed into a Doppler waveform when the Doppler frequency of the clutter overlaps the Doppler frequency of a blood flow or when the Doppler frequency of the clutter is higher than the Doppler frequency of the blood flow. In this case also, it is impossible to display only the blood flow on an FFT display by eliminating clutter. FIG. 3 is a diagram illustrating an example of an FFT display provided when the Doppler frequency of clutter overlaps the Doppler frequency of a blood flow.

FIG. 3 illustrates results of an experiment in which vibrations were applied to the upper side of a blood flow phantom by using a vibrator of a mobile phone. Here, the experiment conditions were: that the flow rate of the blood flow phantom was 1 to 4 cm/s and that the velocity of clutter attributable to vibration of the mobile phone was ±3.8 cm/s. FIG. 3 illustrates a case where, in addition to a Doppler waveform 30a, a color Doppler image 30b was displayed side by side therewith. The Doppler waveform 30a and the color Doppler image 30b were obtained through scanning at different times. Under such experiment conditions, an artifact 30c is displayed all across an ROI in the color Doppler image 30b while the mobile phone vibrates, as illustrated in the right-hand side of FIG. 3. The Doppler waveform 30a in the left-hand side of FIG. 3 is displayed with a blood flow signal and a clutter signal overlapping each other.

Figure 4:
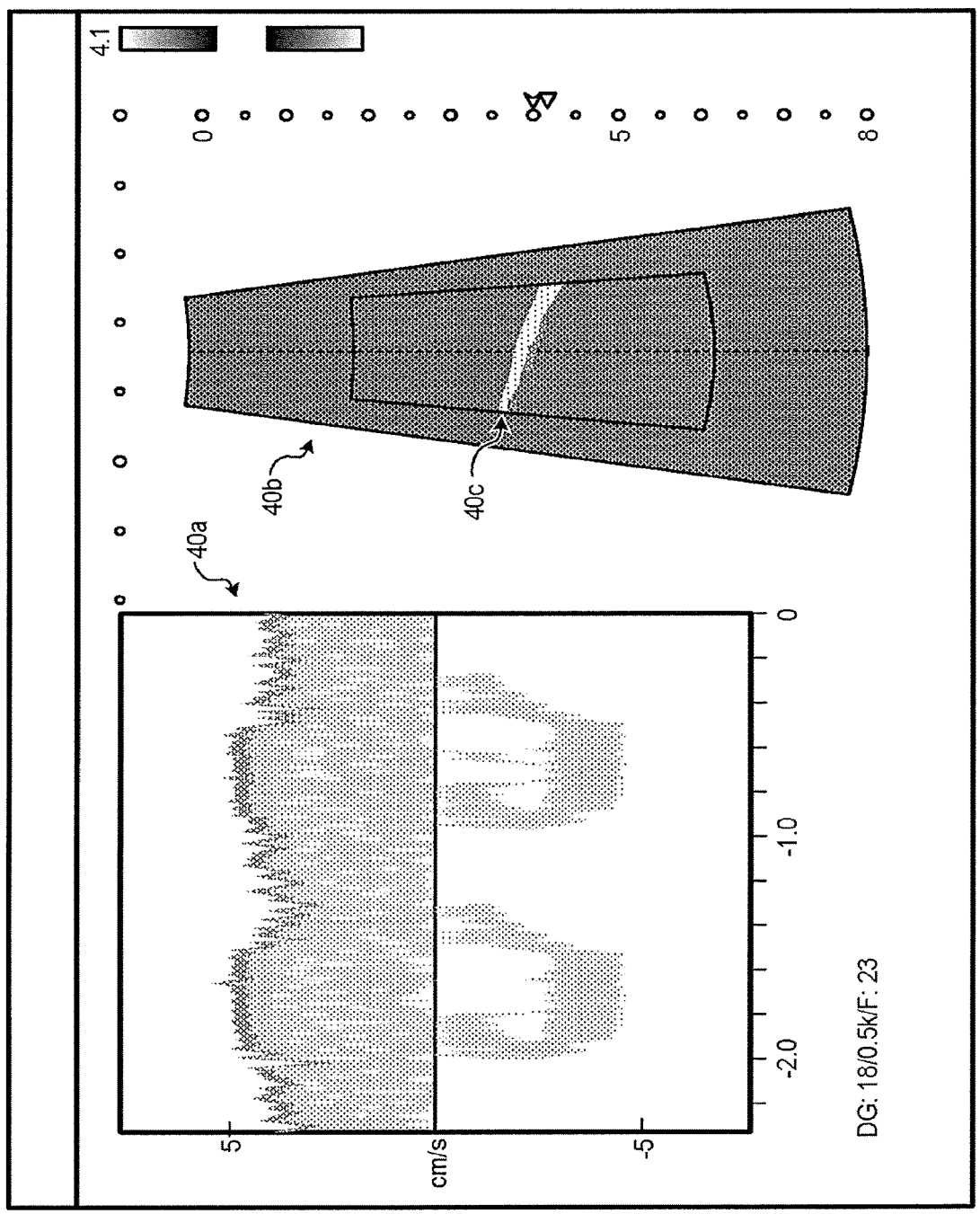
FIG. 4 is a diagram illustrating an example of an FFT display provided when the Doppler frequency of clutter overlaps the Doppler frequency of a blood flow in ultrasound scanning based on the high frame rate method and MTI filter processing using a result of a principal component analysis.

One known method (Japanese Patent Application Laid-open No. 2014-158698) enables execution of ultrasound scanning based on: a method (the high frame rate method) that includes performing transmission and reception of ultrasound waves one time with respect to each of a plurality of scan lines, and acquiring information on the movement of a moving body using echo signals corresponding to a plurality of frames; and MTI filter processing using a result of a principal component analysis. FIG. 4 is a diagram illustrating an example of an FFT display provided when the Doppler frequency of clutter overlaps the Doppler frequency of a blood flow in ultrasound scanning based on the high frame rate method and MTI filter processing using a result of a principal component analysis. In FIG. 4, the experiment conditions are the same as those in FIG. 3 except for the point that the ultrasound scanning is based on the high frame rate method. A Doppler waveform 40a and a color Doppler image 40b were obtained through scanning at different times, and the Doppler waveform 30a in FIG. 3 and the Doppler waveform 40a in FIG. 4 are identical with each other.

When ultrasound scanning is executed as ultrasound scanning based on the high frame rate method, the color Doppler image 40b having only a blood flow signal 40c visualized therein with a clutter signal being weakened can be displayed even when the Doppler frequency of clutter is higher than the Doppler frequency of the blood flow as illustrated in the right-hand side of FIG. 4. Although the vibrator was then vibrating, no artifact was observed in the ROI, and the blood flow was displayed therein. By contrast, even when ultrasound scanning is executed as ultrasound scanning based on the high frame rate method, the blood flow signal and the clutter signal in some cases are displayed overlapping each other, and the blood flow signal cannot be observed, even when the FFT waveform 40a is displayed by the PWD method as illustrated in the left-hand side of FIG. 4.

Given this situation, the PWD processing circuitry 14b executes processing described below, thereby reducing noise and causing only a blood flow to be displayed in an FFT display based on the PWD method, in the first embodiment. Consequently, the ultrasound diagnosis apparatus according to the first embodiment reduces noise and causes only a blood flow to be displayed, for example, when there is a discontinuity in an input data string, when the Doppler frequency of clutter overlaps the Doppler frequency of the blood flow, or when the Doppler frequency of the clutter is higher than the Doppler frequency of the blood flow. In the first embodiment, the processing circuitry 17 is described as being configured to control the transmitter/receiver circuitry 11 so that a plurality of sets of transmission and reception of ultrasound waves are performed on a plurality of scan lines.

Figure 5:
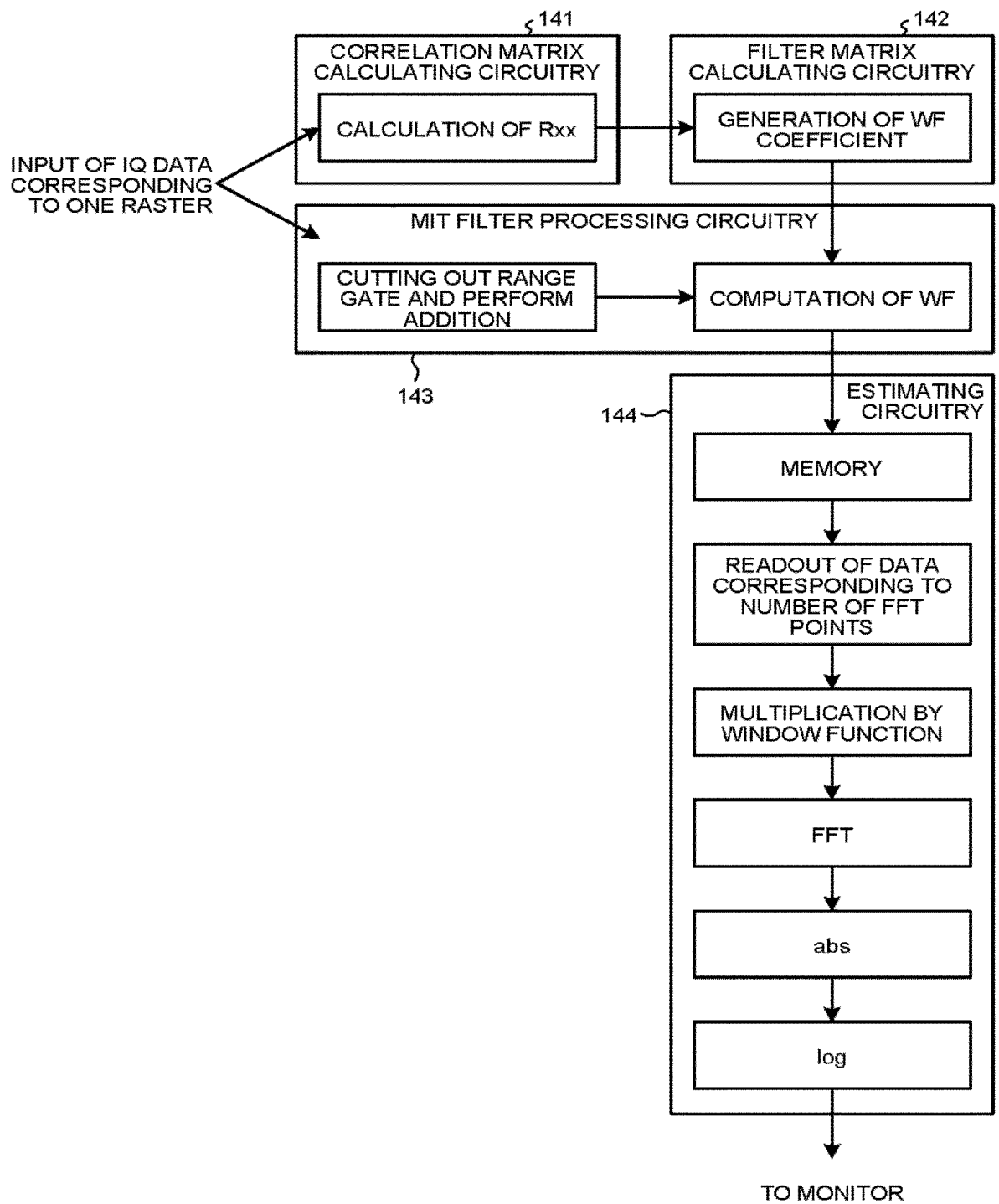
FIG. 5 is a block diagram illustrating an exemplary configuration of PWD processing circuitry according to the first embodiment.

FIG. 5 is a block diagram illustrating an exemplary configuration of the PWD processing circuitry 14b according to the first embodiment. As illustrated in FIG. 5, the PWD processing circuitry 14b includes correlation matrix calculating circuitry 141, filter matrix calculating circuitry 142, MTI filter processing circuitry 143, and estimating circuitry 144. The correlation matrix calculating circuitry 141 calculates a correlation matrix using first data strings, which are sets of echo data generated based on echo signals that occur as a result of transmission of ultrasound waves on the same scan line. Based on a result of a principal component analysis using the correlation matrix, the filter matrix calculating circuitry 142 obtains a filter coefficient that suppresses clutter components. Using the filter coefficient, the MTI filter processing circuitry 143 extracts a second data string from target data strings that are, among the first data strings, contained in an ROI. The second data string is a set of echo data derived from ultrasound echo signals reflected by a moving body present in the ROI. In other words, the MTI filter processing circuitry 143 uses the filter coefficient, thereby obtaining the second data string from the target data strings that are, among the first data strings, contained in the ROI. The second data string is a set of echo data derived from echo signals based on the moving body present in the ROI. The estimating circuitry 144 performs a frequency analysis on the second data string to derive waveform information indicating temporal changes of the moving body. Specific details of processing that the individual units included in the Doppler processing circuitry 14 according to the first embodiment perform are described later.

Figure 6:
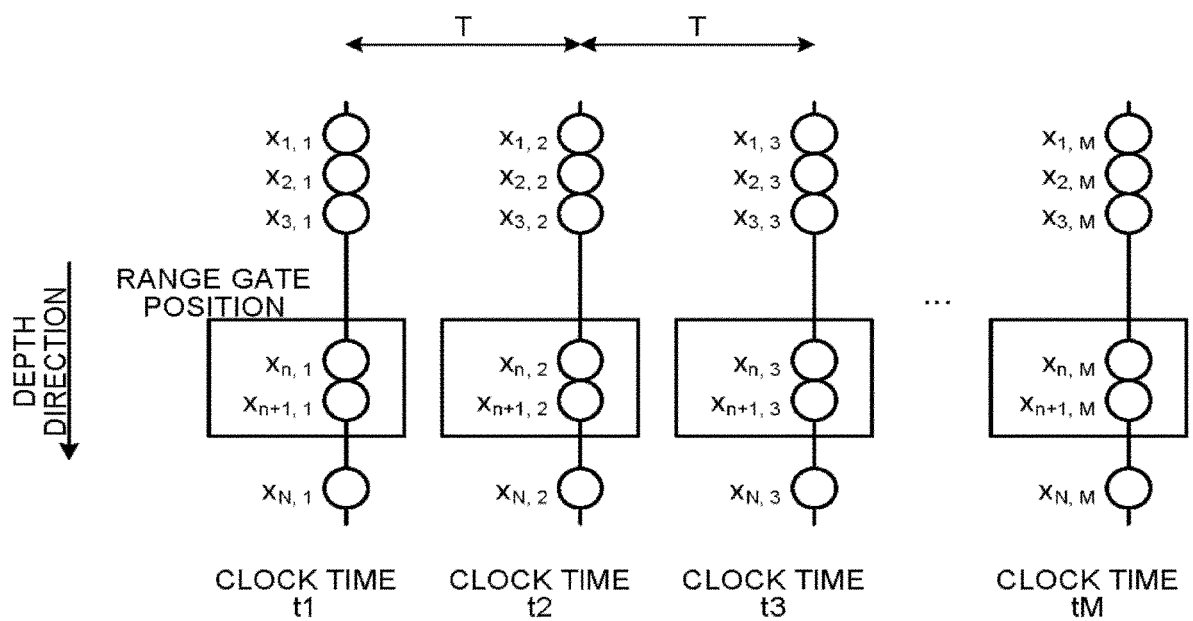
FIG. 6 is a diagram for explaining IQ data that is input to the PWD processing circuitry according to the first embodiment.

As illustrated in FIG. 5, IQ data corresponding to one scan line (raster) is input to the PWD processing circuitry 14b. With reference to FIG. 6, IQ data that is input to the PWD processing circuitry 14b is described. FIG. 6 is a diagram for explaining IQ data that is input to the PWD processing circuitry 14b according to the first embodiment. FIG. 6 illustrates data present on any one raster in a time series.

The number of pieces of data present on this one raster is denoted as N. Data on this raster is repeatedly input at time intervals of T=1/PRF. For example, among the pieces of data at a clock time t1, $x_{1,1}, x_{2,1}, x_{3,1}, \ldots, x_{N,1}$ are contained. Among the pieces of data at a clock time t2, $x_{1,2}, x_{2,2}, x_{3,2}, \ldots, x_{N,2}$ are contained. In the example in FIG. 6, a case where the n-th position and the (n+1)-th position in the depth direction are set as range gate positions is illustrated. IQ data at all positions, including the range gate positions, in the depth direction in one raster is input to the PWD processing circuitry 14b.

Here, if M pieces of the time-series data at the i-th position in the depth direction on the raster are formed into a column vector $x_i$, the column vector $x_i$ is represented by Mathematical Formula (1). In other words, the column vector "$x_i$" represents a data string at a certain scanning position. This column vector $x_i$ has $x_{i,1}, x_{i,2}, \ldots, x_{i,M}$ as its elements.

$$x_i = \begin{pmatrix} x_{i,1} \\ x_{i,2} \\ \vdots \\ x_{i,M} \end{pmatrix} \quad (1)$$

The correlation matrix calculating circuitry 141 calculates a correlation matrix "$R_{xx}$" using Mathematical Formula (2) given below. Here, the correlation matrix calculating circuitry 141 uses, as the first data string, a data string on the scan line on which the ROI has been set. The correlation matrix calculating circuitry 141 calculates a correlation matrix at every time interval of T.

For example, the correlation matrix calculating circuitry 141 uses Mathematical Formula (2) to average data strings that are present at different positions in a space, thereby finding an ensemble average. In other words, using Mathematical Formula (2), the correlation matrix calculating circuitry 141 calculates an autocorrelation matrix of a data string for each of a plurality of sample points, and calculates an average of the autocorrelation matrices for the respective sample points. Here, the index i of $x_i$ denotes a position in a space, and the total number of positions i is set to N. The positions "i" correspond to the positions n in the depth direction in FIG. 6. H denotes transposition (Hermitian transposition) of a matrix formed of complex conjugates of the corresponding elements of a given matrix. The correlation matrix "$R_{xx}$" is formed into a matrix of M rows and M columns from Mathematical Formula (2).

$$R_{xx} = \frac{1}{N}\sum_{i=1}^{N} x_i x_i^H \quad (2)$$

Subsequently, the filter matrix calculating circuitry 142 calculates the filter coefficient, based on a result of a principal component analysis using the correlation matrix. The filter matrix calculating circuitry 142 calculates the filter coefficient at every time interval of T. For example, the filter matrix calculating circuitry 142 performs a principal component analysis using the correlation matrix and performs matrix calculations for approximating clutter components as principal components and suppressing them, thereby calculating the filter coefficient that suppresses clutter from tissue.

More specifically, the filter matrix calculating circuitry 142 calculates eigenvalues and eigenvectors of the matrix $R_{xx}$, which is a matrix of M rows and M columns. A matrix obtained by arranging, as column vectors, the eigenvectors from left in descending order of the corresponding eigenvalues is set to V. When a signal is approximated using the top K principal components and then the resultant approximate signal is subtracted from the original signal, a formula expressed as Mathematical Formula (3) is obtained, where: I denotes an identity matrix; and "$V^H$" denotes a complex conjugate transpose of a matrix of "V".

$$x - V\begin{pmatrix}1 & & & & \\ & 1 & & & \\ & & \ddots & & \\ & & & 0 & \\ & & & & 0\end{pmatrix}V^H x = \left\{I - V\begin{pmatrix}1 & & & & \\ & 1 & & & \\ & & \ddots & & \\ & & & 0 & \\ & & & & 0\end{pmatrix}V^H\right\}x = \left\{VV^H - V\begin{pmatrix}1 & & & & \\ & 1 & & & \\ & & \ddots & & \\ & & & 0 & \\ & & & & 0\end{pmatrix}V^H\right\}x = V\begin{pmatrix}0 & & & & \\ & 0 & & & \\ & & \ddots & & \\ & & & 1 & \\ & & & & 1\end{pmatrix}V^H x \quad (3)$$

Mathematical Formula (3) implies that an MTI filter is formed by multiplying an input data string x by a matrix W given as Mathematical Formula (4). This MTI filter matrix "W" is calculated as a matrix of M rows and M columns from Mathematical Formula (4).

$$W = V\begin{pmatrix}0 & & & & \\ & 0 & & & \\ & & \ddots & & \\ & & & 1 & \\ & & & & 1\end{pmatrix}V^H \quad (4)$$

The number of zeros in a diagonal matrix between V and $V^H$ in the right-hand side of Mathematical Formula (4) is set to K. This is a process for reducing the rank of a matrix, and K is termed the rank cut number herein. Even with the rank cut number K being fixed, the eigenvalues thereof increase as tissue moves, and motion artifacts are therefore removed as far as possible by use of the rank cut number thereof. However, when the movement of tissue is large, the number of eigenvectors corresponding to the movement increases, and it is therefore desirable that the rank cut number be larger. The rank cut number may be changed by the operator using a switch or the like on the apparatus; however, it is more suitable that the rank cut number be adaptively changed based on the sizes of eigenvalues.

For example, the filter matrix calculating circuitry 142 determines the number of principal components to be cut out, that is, the value of the rank cut number, based on a previously set value or a value designated by the operator. However, when a scanning range contains tissue, such as a heart and a blood vessel, the moving velocity of which changes over time by pulsation, it is suitable that the value of the rank cut number be adaptively determined based on the sizes of eigenvalues. That is, in accordance with the sizes of eigenvalues of the correlation matrix, the filter matrix calculating circuitry 142 changes the number of principal components to be cut out. In the present embodiment, in accordance with the sizes of the eigenvalues, the filter matrix calculating circuitry 142 changes the rank number to which the rank is reduced.

Figures 7, 8:
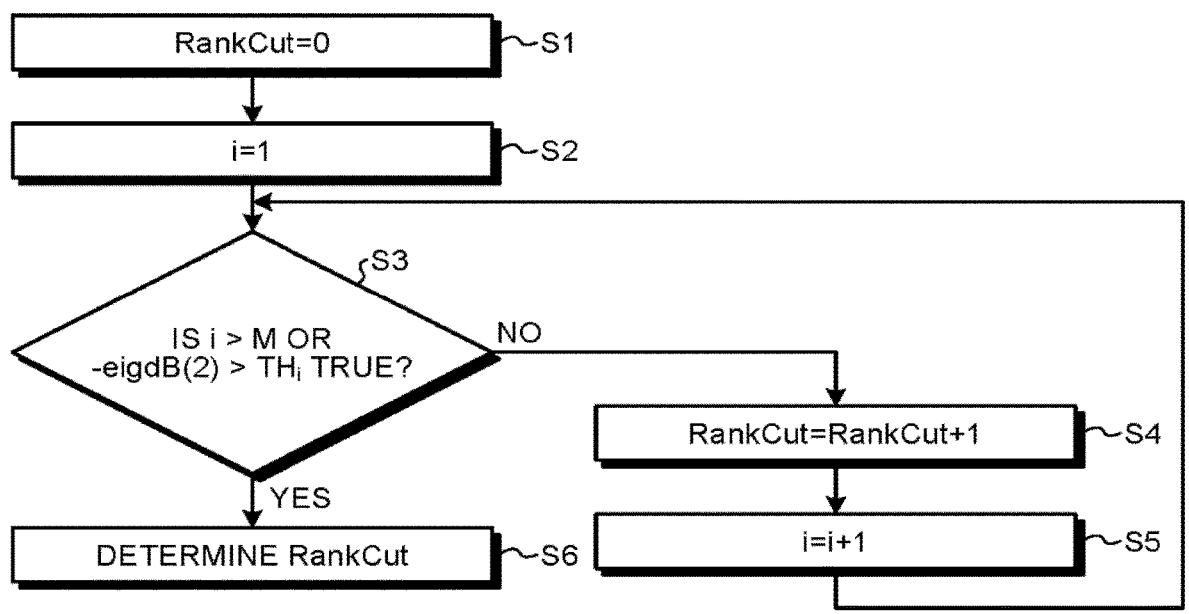
FIG. 7 is a diagram for explaining an example of processing for determining a rank cut number according to the first embodiment.
FIG. 8 is a diagram for explaining an example of processing for determining a rank cut number according to the first embodiment.

The logic for adaptively determining the rank cut number based on the sizes of eigenvalues needs to be optimized in accordance with the site on which ultrasound scanning is performed. For example, the filter matrix calculating circuitry 142 determines the rank cut number using thresholds listed in FIG. 7 and an algorithm illustrated in FIG. 8. The algorithm illustrated in FIG. 8 is an algorithm that determines the rank cut number based on a value obtained by dividing the second largest eigenvalue by the largest eigenvalue. FIG. 7 and FIG. 8 are diagrams for explaining an example of the processing for determining the rank cut number according to the first embodiment.

At the start, the filter matrix calculating circuitry 142 defines, as "eig(k)", the k-th eigenvalue in a sequence of the eigenvalues of the correlation matrix "$R_{xx}$" arranged in descending order of the sizes thereof. "k" is an integer such that $1 \leq k \leq M$. The filter matrix calculating circuitry 142 then calculates "eigdB(k)", which is a value obtained by dividing the k-th largest eigenvalue by the largest eigenvalue "eig(1)" and expressed in units of dB, using Mathematical Formula (5) given below.

$$\text{eigdB}(k) = 10 * \log_{10}(\text{abs}(\text{eig}(k))/\text{abs}(\text{eig}(1))) \quad (5)$$

In Mathematical Formula (5), "abs" is a function for computing the absolute value. In Mathematical Formula (5), "eigdB(2)" when k=2 is a value obtained by dividing the second largest eigenvalue by the largest eigenvalue "eig(1)" and expressed in units of dB.

The filter matrix calculating circuitry 142 uses M thresholds ($TH_i$ where $1 \leq i \leq M$) for use in determining the rank cut number because it obtains M eigenvalues. $TH_i$ is set to a variable that changes depending on the value of i. For example, when M=8, the 8 thresholds "$TH_1$ to $TH_8$" are set as illustrated in FIG. 7. In FIG. 7, $TH_1$ and $TH_2$ are set to "1000000 dB". In FIG. 7, $TH_3$ is set to "20 dB", and $TH_4$ is set to "15 dB". In FIG. 7, $TH_5$ is set to "10 dB", and $TH_6$ is set to "5 dB". In FIG. 7, $TH_7$ and $TH_8$ are set to "−1 dB". When the thresholds illustrated in FIG. 7 are used, the algorithm in FIG. 8 described below gives a value not less than 2 and not more than 6 as the rank cut number. In FIG. 8, the rank cut number is denoted by "RankCut".

At the start, the filter matrix calculating circuitry 142 sets "RankCut=0" (Step S1), and sets "i=1" (Step S2). The filter matrix calculating circuitry 142 then determine whether at least one of the following is true: that "i" exceeds "L"; and that "−eigdB(2)" exceeds "$TH_i$" (Step S3). Here, if "i" is not more than "L" and "−eigdB(2)" is not more than "$TH_1$" (No at Step S3), the filter matrix calculating circuitry 142 sets RankCut=RankCut+1 by incrementing the rank cut number (Step S4).

Subsequently, the filter matrix calculating circuitry 142 sets "i=i+1" (Step S5), and then performs determination processing at Step S3. Here, for example, "−eigdB(2)" that is used in the determination processing at Step S3 after the processing at Step S5 performed for the first time is a value obtained by multiplying a first value by "−1". The first value is obtained in such a manner that: a second sequence is obtained by excluding the largest eigenvalue from a first sequence of L eigenvalues arranged in descending order of the sizes thereof; the second largest eigenvalue in the second sequence is divided by the largest eigenvalue in the second sequence "eig(1)"; the result of the division is expressed in units of dB; and the result expressed in units of dB is multiplied by "−1".

On the other hand, if "i" exceeds "M" or if "−eigdB(2)" exceeds "$TH_i$" (Yes at Step S3), the filter matrix calculating circuitry 142 determines the last updated "RankCut" to be an amount by which the rank number is reduced (Step S6). For example, the filter matrix calculating circuitry 142 determines the rank cut number to be 4 when eigdB(2)=−12 dB under the conditions listed in FIG. 7.

The algorithm that adaptively determines the rank cut number based on the sizes of eigenvalues are not limited to the above algorithm, and can be implemented as any one of various algorithms. These algorithms can be selectively used for imaging different sites, for example.

The filter matrix calculating circuitry 142 determines the rank cut number for each display frame using the algorithm illustrated in FIG. 8, and calculates the MTI filter matrix "W".

Using the filter coefficient, the MTI filter processing circuitry 143 extracts a second data string from target data strings that are, among the first data strings, contained in a range gate. The second data string is a set of echo data derived from ultrasound echo signals reflected by a moving body present in the range gate. The MTI filter processing circuitry 143 extracts a second data string at every time interval of T. Here, a range of positions that an FFT analysis covers is set as the range gate by a user. The MTI filter processing circuitry 143 adds up signals within this range thus set as the range gate. In the example illustrated in FIG. 6, the n-th piece and the (n+1)-th piece of data are contained in the range set as the range gate, and MTI filter processing circuitry 143 takes out these two pieces, or the n-th piece and the (n+1)-th piece, of the data for adding. Mathematical Formula (6) expresses y, which denotes the time-series vector after the adding.

$$y = x_n + x_{n+1} \tag{6}$$

The MTI filter processing circuitry 143 performs filter processing on the time-series vector y after the adding. Here, Mathematical Formula (7) expresses z, which denotes the column vector to be output after the filter processing.

$$z = Wy \tag{7}$$

Figure 9:
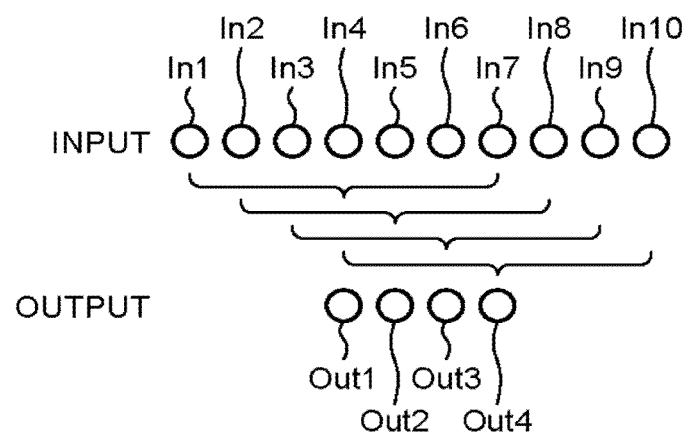
FIG. 9 is a diagram for explaining processing operations that MTI filter processing circuitry according to the first embodiment performs.

The MTI filter processing circuitry 143 outputs, as pieces of data that form the second data string, a certain number of pieces of data in an output data string obtained by processing an input target data string with the filter coefficient. FIG. 9 is a diagram for explaining processing operations that the MTI filter processing circuitry 143 according to the first embodiment performs. For example, the MTI filter processing circuitry 143 selects one (M/the second element) at the center of an output vector z obtained by the filter processing, and outputs the selected element to the estimating circuitry 144.

More specifically, the MTI filter processing circuitry 143 receives input of In1 to In7 as a target data string at a clock time t1, as illustrated in FIG. 9, for example. The MTI filter processing circuitry 143 then performs filter processing on the target data strings (In1 to In7) using the MTI filter matrix "W" calculated by the filter matrix calculating circuitry 142. In this case, the correlation matrix calculating circuitry 141 calculates a correlation matrix "$R_{xx}$" from IQ signals that are on the same scan lines as the target data strings In1 to In7, and the filter matrix calculating circuitry 142 calculates the MTI filter matrix "W" based on a result of a principal component analysis using the correlation matrix "$R_{xx}$" calculated from IQ signals that are on the same scan lines as the target data strings In1 to In7.

Subsequently, the MTI filter processing circuitry 143 selects, for example, the fourth element from the data string on which the filter processing has been performed, and outputs, as Out1, the selected element to the estimating circuitry 144, as illustrated in FIG. 9. As a result, the estimating circuitry 144 stores the received data in a memory.

After performing filter processing on one target data string, the MTI filter processing circuitry 143 further performs filter processing on a new target data string. For example, the MTI filter processing circuitry 143 receives input of In2 to In8 as a target data string, for example, at a clock time t2, and performs MTI filter processing, as illustrated in FIG. 9. That is, the MTI filter processing circuitry 143 performs MTI filter processing on the data strings In2 to In8 as target data strings at the clock time t2. The data strings In2 to In8 are shifted by one piece of data from the target data strings In1 to In7 already subjected to MTI filter processing at the clock time t1. In other words, the MTI filter processing circuitry 143 performs MTI filter processing at every time interval of T on a target data string obtained by shifting the previous data string by one piece of data.

Subsequently, the MTI filter processing circuitry 143 selects, for example, the fourth element from the data string on which the MTI filter processing has been performed, and outputs, as Out2, the selected element to the estimating circuitry 144, as illustrated in FIG. 9. In this case, the correlation matrix calculating circuitry 141 calculates a correlation matrix "$R_{xx}$" from IQ signals that are on the same scan lines as the target data strings In2 to In8, and the filter matrix calculating circuitry 142 calculates the MTI filter matrix "W" based on a result of a principal component analysis using the correlation matrix "$R_{xx}$" calculated from IQ signals that are on the same scan lines as the target data strings In2 to In8. The MTI filter processing circuitry 143 thus outputs, as pieces of data that form the second data string, a certain number of pieces of data in an output data string obtained by performing MTI filter processing with the MTI filter matrix "W" on an input target data string. After performing MTI filter processing on one target data string, the MTI filter processing circuitry 143 further performs filter processing on a new target data string.

The estimating circuitry 144 performs a frequency analysis on the second data string to derive the waveform information. Here, for example, when data output as data forming the second data strings has accumulated to correspond to the number of points for a frequency analysis, the estimating circuitry 144 performs the frequency analysis on the second data strings to derive waveform information. More specifically, the estimating circuitry 144 stores data received from the MTI filter processing circuitry 143 in a memory, and determines whether the received data has accumulated to correspond to the number of FFT points.

Here, upon determining that the data has not accumulated to correspond to the number of FFT points, the estimating circuitry 144 continues repeating the determination processing. On the other hand, upon determining that data has accumulated to correspond to the number of FFT points, the estimating circuitry 144 performs the frequency analysis on the second data strings to derive waveform information. For example, the estimating circuitry 144 loads data corresponding to the number of FFT points from a memory, multiplies the data by a window function, and then performs FFT computation. Subsequently, the estimating circuitry 144 obtains the absolute values and performs logarithmic compression to generate an FFT waveform, and then output the resultant data to the monitor 2.

Figure 10:
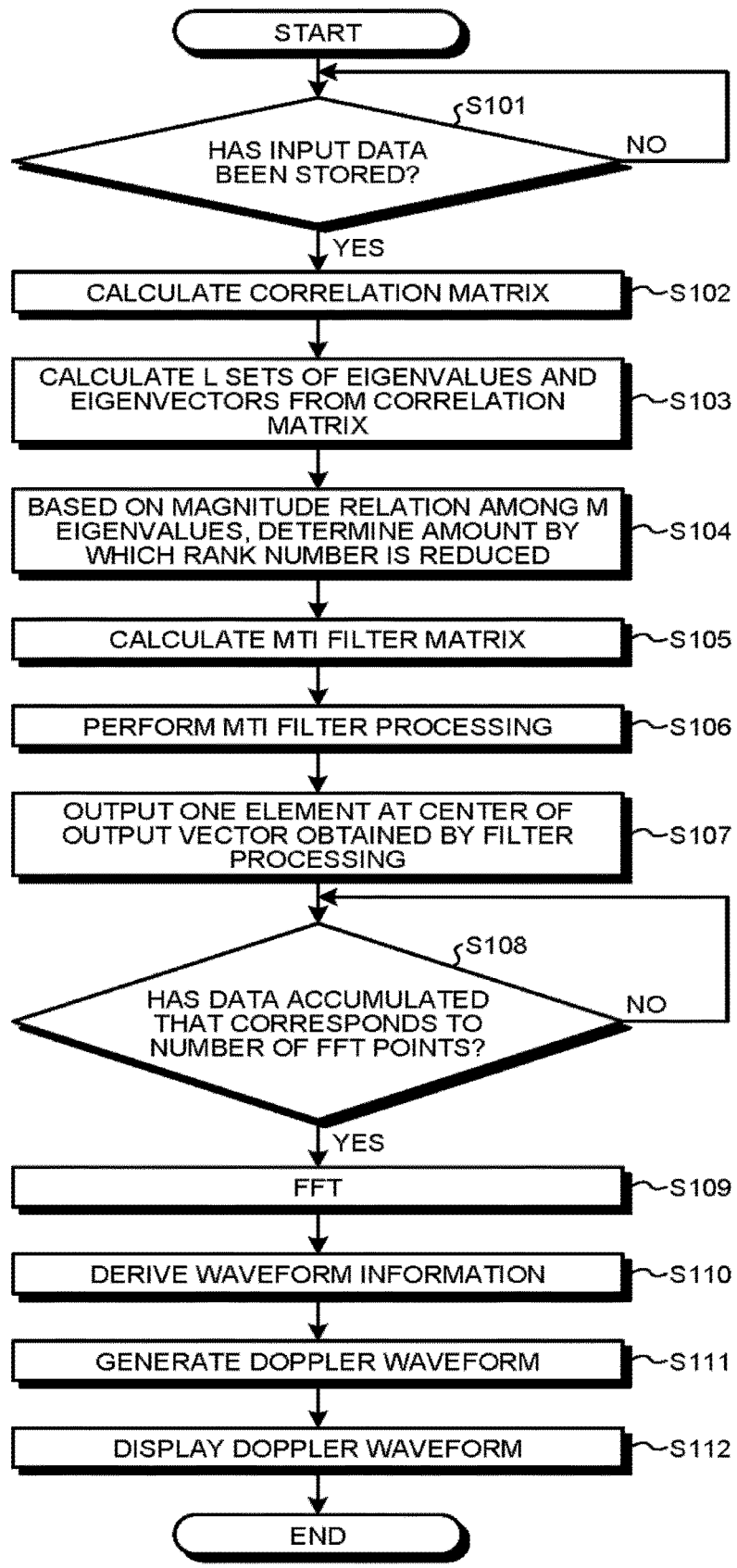
FIG. 10 is a flowchart for explaining an example of processing that the ultrasound diagnosis apparatus according to the first embodiment performs.

With reference to FIG. 10, the following describes an example of processing that the ultrasound diagnosis apparatus according to the first embodiment performs. FIG. 10 is a flowchart for explaining the example of processing that the ultrasound diagnosis apparatus according to the first embodiment performs. The flowchart illustrated in FIG. 10 is a flowchart that explains processing that the ultrasound diagnosis apparatus according to the first embodiment performs for generating and displaying a Doppler waveform with the application of the PWD method.

As illustrated in FIG. 10, the processing circuitry 17 in the ultrasound diagnosis apparatus according to the first embodiment first determines whether data strings the number of which corresponds to the processing to be performed have been input (Step S101). Here, upon determining that data strings the number of which corresponds to processing to be performed (Yes at Step S101), the processing circuitry 17 proceeds to Step S102. On the other hand, upon not determining that data strings the number of which corresponds to processing to be performed (No at Step S101), the processing circuitry 17 repeatedly executes Step S101.

Subsequently, the correlation matrix calculating circuitry 141 calculates a correlation matrix on a scan line (Step S102), and the filter matrix calculating circuitry 142 calculates M sets of eigenvalues and eigenvectors from the correlation matrix (Step S103). In the illustration in FIG. 10, the correlation matrix calculating circuitry 141 calculates a correlation matrix at every time interval of T, and the filter matrix calculating circuitry 142 calculates M sets of eigenvalues and eigenvectors from the correlation matrix at every time interval of T.

The filter matrix calculating circuitry 142 then determines, based on the magnitude relation among the M eigenvalues, the amount by which the rank number is reduced (Step S104) and calculates an MTI filter matrix (Step S105). The MTI filter processing circuitry 143 then performs MTI filter processing (Step S106). The MTI filter processing circuitry 143 outputs one element at the center of an output vector obtained by the filter processing (Step S107). In the example illustrated in FIG. 10, the MTI filter processing circuitry 143 performs the MTI filter processing at every time interval of T.

Subsequently, the estimating circuitry 144 determines whether data has accumulated that corresponds to the number of FFT points (Step S108). Here, upon not determining that data corresponding to the number of FFT points has accumulated (No at Step S108), the estimating circuitry 144 repeats the determination processing at Step S108. On the other hand, upon determining that data corresponding to the number of FFT points has accumulated (Yes at Step S108), the estimating circuitry 144 performs FFT using the output data output from the MTI filter processing (Step S109). The estimating circuitry 144 then derives waveform information indicating the temporal changes of the moving body from a result of the FFT (Step S110).

Figure 11:
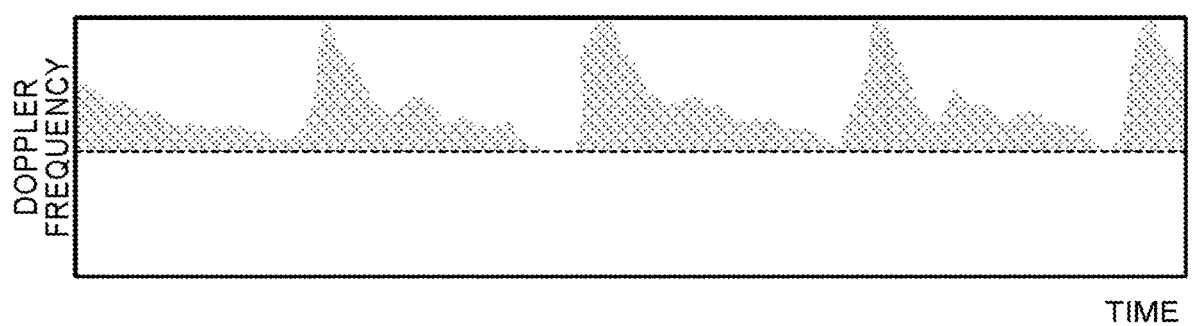
FIG. 11 is a diagram illustrating an example of an FFT waveform according to the first embodiment.

Subsequently, the image generating circuitry 15 generates a Doppler waveform from the waveform information (Step S111), and the monitor 2 displays thereon the Doppler waveform under the control of the processing circuitry 17 (Step S112), which ends the processing. FIG. 11 is a diagram illustrating an example of an FFT waveform according to the first embodiment.

FIG. 11 illustrates an example of an FFT display provided when a discontinuity has occurred in an input data string, as in FIG. 2A and FIG. 2B. As illustrated in FIG. 11, the clutter observed as spanning wide Doppler frequency ranges as indicated by the arrows in FIG. 2A and FIG. 2B was removed. Consequently, only a blood flow signal the frequency of which overlaps a frequency attributable to clutter can be thus displayed.

As described above, in the first embodiment, noise reduction in FFT display according to the PWD method is enabled.

Modification 1 of First Embodiment

In the first embodiment described above, the case where IQ data corresponding to one raster is used as input is described. It is preferable that a relatively wide region be used for calculating the correlation matrix $R_{xx}$. For this reason, when a plurality of reception rasters can be acquired from one set of transmission, the correlation matrix calculating circuitry 141 may input IQ data corresponding to the reception rasters to be used for calculation of $R_{xx}$. In other words, the correlation matrix calculating circuitry 141 uses, as the first data strings, data strings on a plurality of scan lines including at least a scan line on which the region of interest has been set.

Modification 2 of First Embodiment

Figure 12A:
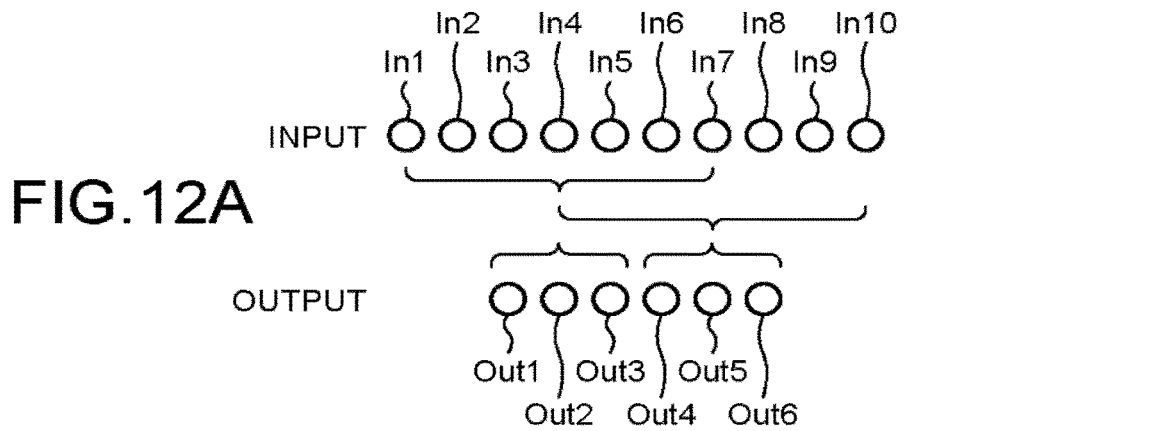
FIG. 12A is a diagram for explaining Modification 2 of the first embodiment.
Figure 12B:
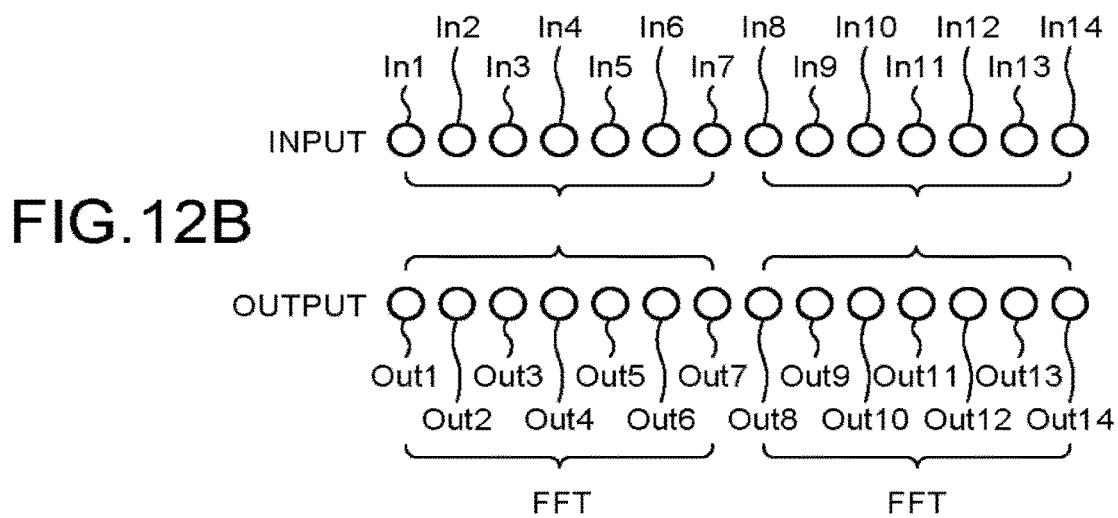
FIG. 12B is another diagram for explaining Modification 2 of the first embodiment.
Figure 12C:
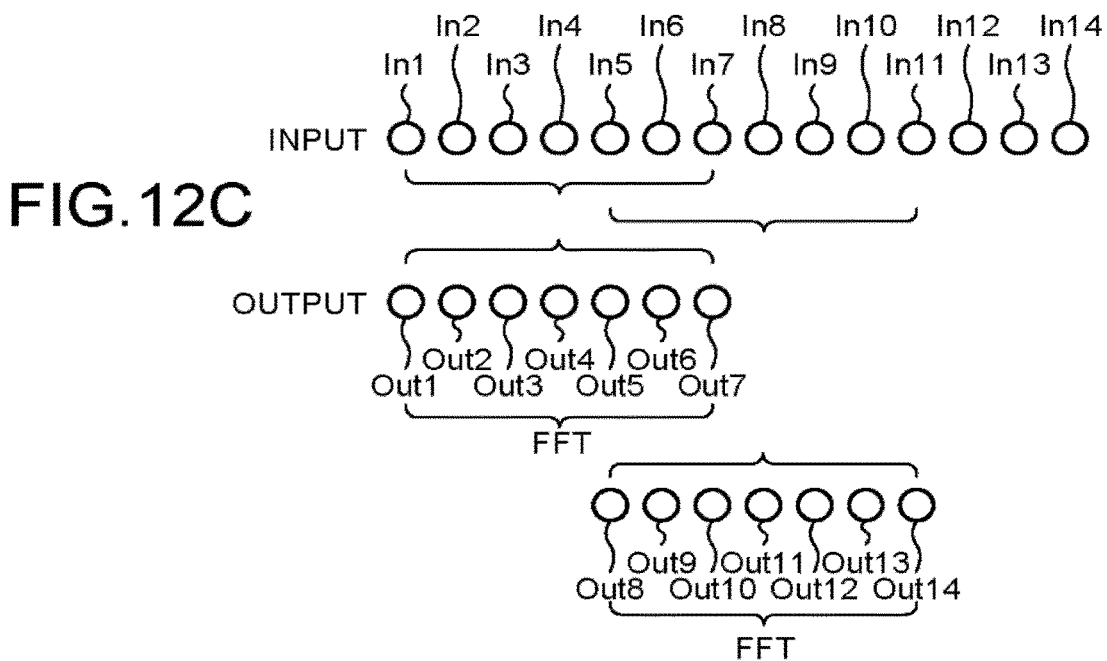
FIG. 12C is still another diagram for explaining Modification 2 of the first embodiment.

Although the case of outputting one element at the center of the output vector z obtained through the MTI filter as illustrated in FIG. 9 is described in the first embodiment described above, the embodiment is not limited thereto. For example, the MTI filter processing circuitry 143 may output P elements at the center. In addition, although the MTI filter processing circuitry 143 is described as being configured to perform MTI filter processing at every time interval of T on a target data string obtained by shifting the previous data string by one piece of data, the embodiment is not limited thereto. For example, the MTI filter processing circuitry 143 may perform MTI filter processing at every time interval of T on a target data string obtained by shifting the previous data string by a plurality of pieces of data. In other words, the data length of a target data string (the width of the MTI filter) and the number of overlapping pieces of data (the number of pieces of data by which the data is shifted) in this and the next target data strings may be determined in advance. Modification 2 of the first embodiment is described with reference to FIGS. 12A to 12C. FIGS. 12A to 12C are diagrams for explaining Modification 2 of the first embodiment. Hereinafter, the number of pieces of data by which the data string is shifted after MTI filter processing to obtain a new target data string is referred to as the shift amount S.

FIG. 12A illustrates a case where the width of the MTI filter is 7 and S=3. For example, at a clock time t1, the MTI filter processing circuitry 143 receives input of In1 to In7 as a target data string and performs MTI filter processing thereon, as illustrated in FIG. 12A. The MTI filter processing circuitry 143 then selects, for example, the third to the fifth elements in a data string obtained by the MTI filter processing and outputs these elements as Out1 to Out3 to the estimating circuitry 144, as illustrated in FIG. 12A.

After the elapse of time intervals of 3T, for example, at a clock time t4, the MTI filter processing circuitry 143 receives input of In4 to In10 as a target data string and performs MTI filter processing thereon, as illustrated in FIG. 12A. The MTI filter processing circuitry 143 then selects, for example, the third to the fifth elements in a data string obtained by the MTI filter processing and outputs these elements as Out4 to Out6 to the estimating circuitry 144, as illustrated in FIG. 12A.

In this case, the amount of calculation of a correlation matrix $R_{xx}$ can be reduced to $1/M^2$ in the correlation matrix calculating circuitry 141, and the amount of calculation of an MTI filter matrix "W" can be reduced to $1/M^2$ in the filter matrix calculating circuitry 142. Calculating $R_{xx}$ and calculating an MTI filter matrix "W" are both matrix calculation, and the amount of calculation is reduced to $1/M^2$ if the numbers of rows and columns are both reduced to $1/M$. Consequently, the processing for generating an FFT waveform can be thus speeded up.

FIG. 12B illustrates a case where the width of the MTI filter is 7 and S=7. That is, in FIG. 12B, the width of the MTI filter, the number of data output points, the number of FFT points, and the shift amount of the time-series data are all set to the same number. For example, at a clock time t1, the MTI filter processing circuitry 143 receives input of In1 to In7 as a target data string and performs MTI filter processing thereon, as illustrated in FIG. 12B. The MTI filter processing circuitry 143 then selects all of the elements in a data string obtained by the MTI filter processing and outputs these elements as Out1 to Out7 to the estimating circuitry 144, as illustrated in FIG. 12B.

After the elapse of time intervals of 7T, for example, at a clock time t8, the MTI filter processing circuitry 143 receives input of In8 to In14 as a target data string and performs MTI filter processing thereon, as illustrated in FIG. 12B. The MTI filter processing circuitry 143 then selects all of the elements in a data string obtained by the MTI filter processing and outputs these elements as Out8 to Out14 to the estimating circuitry 144, as illustrated in FIG. 12B. In the case illustrated in FIG. 12B, output vectors obtained using the MTI filter are all used, and there is no useless part in the processing. Consequently, speeding up of the processing and accuracy of the frequency analysis can be both accomplished. Although the width of the MTI filter, the number of data output points, the number of FFT points, and the shift amount of the time-series data are all set to the same number in FIG. 12B, the shift amount of the time-series data can be set to a number smaller or larger than the numbers of the others. The sweep speed of an FFT image can be thus adjusted.

FIG. 12C illustrates a case where the width of the MTI filter is 7 and S=4. For example, at a clock time t1, the MTI filter processing circuitry 143 receives input of In1 to In7 as a target data string and performs MTI filter processing thereon, as illustrated in FIG. 12C. The MTI filter processing circuitry 143 then selects all of the elements in a data string obtained by the MTI filter processing and outputs these elements as Out1 to Out7 to the estimating circuitry 144, as illustrated in FIG. 12C.

After the elapse of time intervals of 4T, for example, at a clock time t5, the MTI filter processing circuitry 143 receives input of In5 to In11 as a target data string and performs MTI filter processing thereon, as illustrated in FIG. 12C. The MTI filter processing circuitry 143 then selects all of the elements in a data string obtained by the MTI filter processing and outputs these elements as Out8 to Out14 to the estimating circuitry 144, as illustrated in FIG. 12C. Also in the case illustrated in FIG. 12C, output vectors obtained using the MTI filter are all used, and there is no useless part in the processing. Consequently, speeding up of the processing and accuracy of the frequency analysis can be both accomplished.

Second Embodiment

Figure 13:
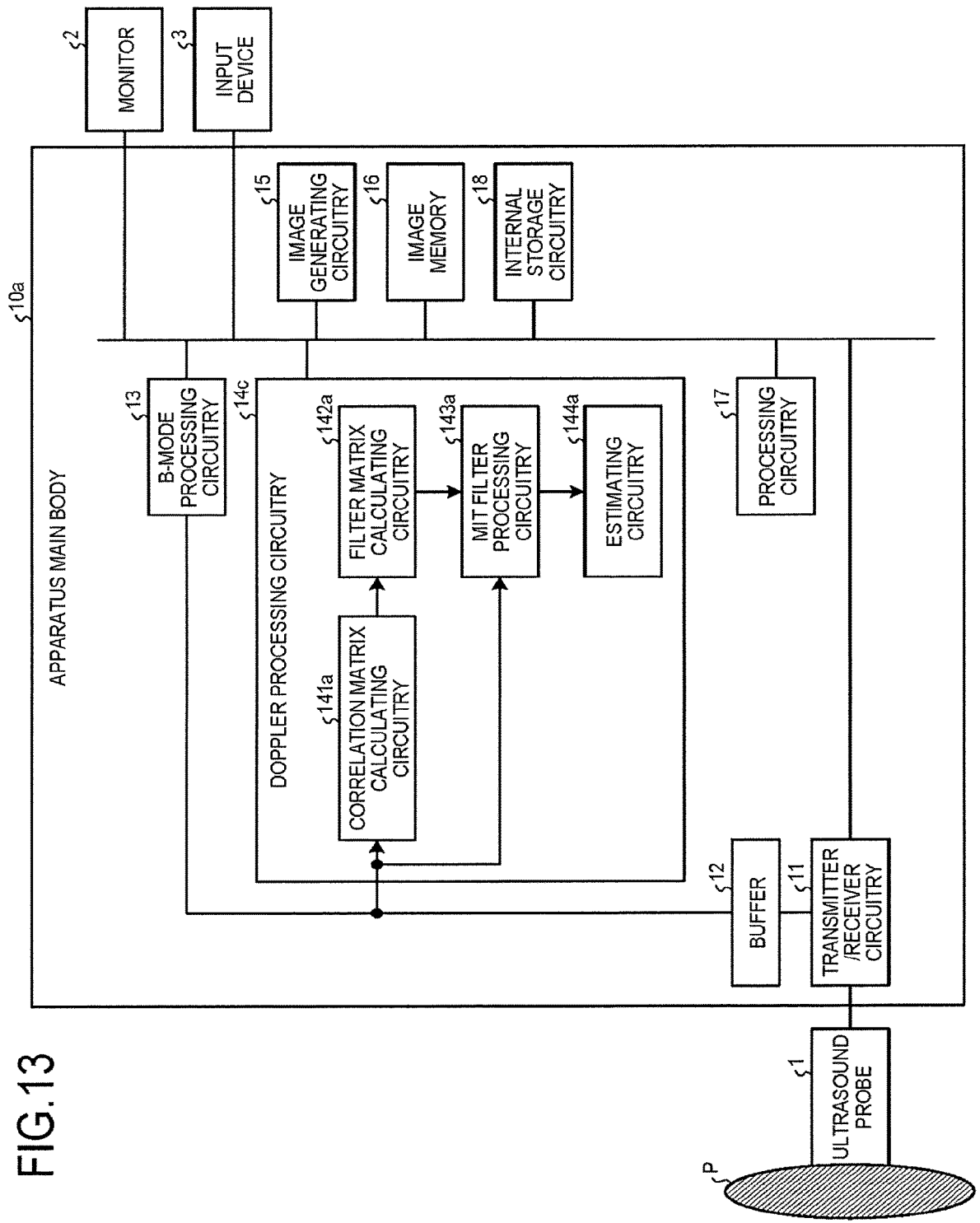
FIG. 13 is a diagram for explaining an exemplary configuration of an ultrasound diagnosis apparatus according to a second embodiment.

A second embodiment describes a case where data strings of continuous echo data from the same position are acquired by repeating a scanning form in which transmission and reception of ultrasound waves are executed one time on each scan line in a scanning range. FIG. 13 is a diagram for explaining an exemplary configuration of an ultrasound diagnosis apparatus according to the second embodiment. In FIG. 13, the same signs are assigned to components that are the same as the units included in the ultrasound diagnosis apparatus according to the first embodiment illustrated in FIG. 1, and detailed descriptions thereof are omitted.

As illustrated in FIG. 13, the ultrasound diagnosis apparatus according to the second embodiment includes an ultrasound probe 1, a monitor 2, an input device 3, and an apparatus main body 10a. The apparatus main body 10a according to the second embodiment is an apparatus that generates ultrasound images based on echo signals received by the ultrasound probe 1. The apparatus main body 10a includes, as illustrated in FIG. 1, transmitter/receiver circuitry 11, a buffer 12, B-mode processing circuitry 13, Doppler processing circuitry 14c, image generating circuitry 15, an image memory 16, processing circuitry 17, and internal storage circuitry 18.

Figure 14:
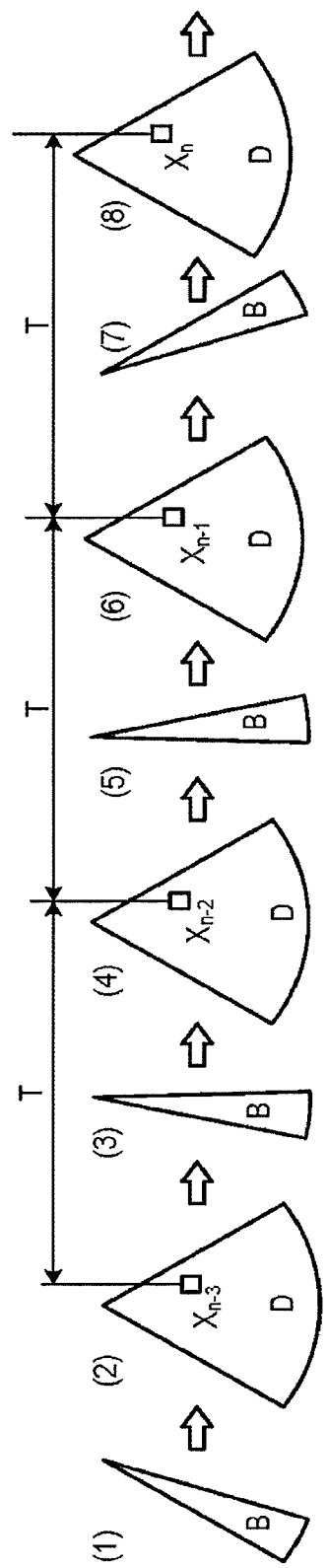
FIG. 14 is a diagram illustrating an example of ultrasound scanning according to the second embodiment.

With reference to FIG. 14, the following describes the ultrasound scanning (the high frame rate method) according to the second embodiment. FIG. 14 is a diagram illustrating an example of ultrasound scanning according to the second embodiment. For example, based on instructions from an operator, initially set information, or the like, the processing circuitry 17 divides a second scanning range into four divided ranges (first to four divided ranges). "B" illustrated in FIG. 14 indicates a range across which ultrasound scanning is being performed under transmission and reception conditions for the B mode. "D" illustrated in FIG. 8 indicates a range across which ultrasound scanning is being performed under transmission and reception conditions for the color Doppler mode. For example, "D" illustrated in FIG. 14 is a range across which ultrasound scanning according to the above high frame rate method is being performed. That is, in first ultrasound scanning illustrated in FIG. 14, transmission and reception of ultrasound waves is performed one time on each scan line unlike in the case of the color Doppler method commonly practiced in which ultrasound waves are transmitted a plurality of times in the same direction and echo signals are received a plurality of times. In other words, the processing circuitry 17 causes, ultrasound scanning to be, as the first ultrasound scanning, executed in which Doppler image data of a blood flow is acquired. The processing circuitry 17 then causes ultrasound scanning to be, as the first ultrasound scanning, executed that is based on a method for acquiring information on a moving body by performing high-pass filter processing (for example, the IIR filter processing) in a direction of frames on received signals (echo data) acquired from a plurality of scan lines forming a first scanning range. The processing circuitry 17 according to the second embodiment causes ultrasound scanning to be, as the first ultrasound scanning, executed that is based on a method for acquiring data strings in a direction of frames along which high-pass filter processing is performed, the method including performing transmission and reception of ultrasound waves one time for each scan line and acquiring reception signals from each of a plurality of scan lines that form the first scanning range. That is, the processing circuitry 17 according to the second embodiment causes ultrasound scanning to be, as the first ultrasound scanning, executed that is based on a method (the high frame rate method) for performing transmission and reception of ultrasound waves one time with respect to each of a plurality of scan lines that form the first scanning range and acquiring information on the movement of a moving body using echo signals corresponding to a plurality of frames.

First, the processing circuitry 17 causes ultrasound scanning on the first divided range to be executed as second ultrasound scanning (see (1) in FIG. 14), and causes the first ultrasound scanning on the second scanning range (corresponding to one frame) to be executed (see (2) in FIG. 14). The processing circuitry 17 then causes ultrasound scanning on the second divided range to be executed as the second ultrasound scanning (see (3) in FIG. 14), and causes the first ultrasound scanning on the second scanning range (corresponding to one frame) to be executed (see (4) in FIG. 14). The processing circuitry 17 then causes ultrasound scanning on the third divided range to be executed as the second ultrasound scanning (see (5) in FIG. 14), and causes the first ultrasound scanning on the second scanning range (corresponding to one frame) to be executed (see (6) in FIG. 14). The processing circuitry 17 then causes ultrasound scanning on the fourth divided range to be executed as the second ultrasound scanning (see (7) in FIG. 14), and causes the first ultrasound scanning on the second scanning range (corresponding to one frame) to be executed (see (8) in FIG. 14).

Here, as illustrated in FIG. 14, the processing circuitry 17 causes the first ultrasound scanning to be performed at uniform intervals. That is, a "point X" on a "certain scan line" in the first scanning range is scanned one time each in the first ultrasound scanning of (2), (4), (6), and (8) in FIG. 14, and each time interval between the first ultrasound scanning is controlled so as to be constant as "T". Specifically, the processing circuitry 17 equalizes time periods to be taken for scanning for the respective divided ranges performed in the second ultrasound scanning, thereby equalizing the time intervals at which the first ultrasound scanning is performed. For example, the processing circuitry 17 performs control so that time periods to be taken for scanning for the respective divided ranges in the second ultrasound scanning performed in (1), (3), (5), and (7) in FIG. 14 can be exactly the same. The processing circuitry 17 equalizes the sizes, the numbers of scan lines, the scan line densities, the depths, and the like of the respective divided ranges obtained by dividing the second scanning range. For example, time periods to be taken for scanning for the respective divided ranges in the second ultrasound scanning are the same when the numbers of scan lines thereof are the same. The Doppler processing circuitry 14 outputs motion information on a blood flow at the "point X" by performing the above IIR filter processing on a data string ($X_{n-3}$, $X_{n-2}$, $X_{n-1}$, and $X_n$) at the same position in frames for "D", as illustrated in FIG. 14.

As described above, in the second embodiment, conditions for transmission and reception of ultrasound waves can be set independently in the first ultrasound scanning and the second ultrasound scanning. Therefore, gains of a preamplifier can be separately optimized in the first ultrasound scanning and the second ultrasound scanning, and saturation of echo signals from tissue can be consequently avoided.

In addition, the second ultrasound scanning is performed as scanning for the divided ranges during the first ultrasound scanning corresponding to one frame, so that the magnitude of reduction in frame rate that occurs as a result of performing the second ultrasound scanning corresponding to one frame can be kept down. Consequently, the aliasing velocity of the blood flow can be increased.

Figure 15:
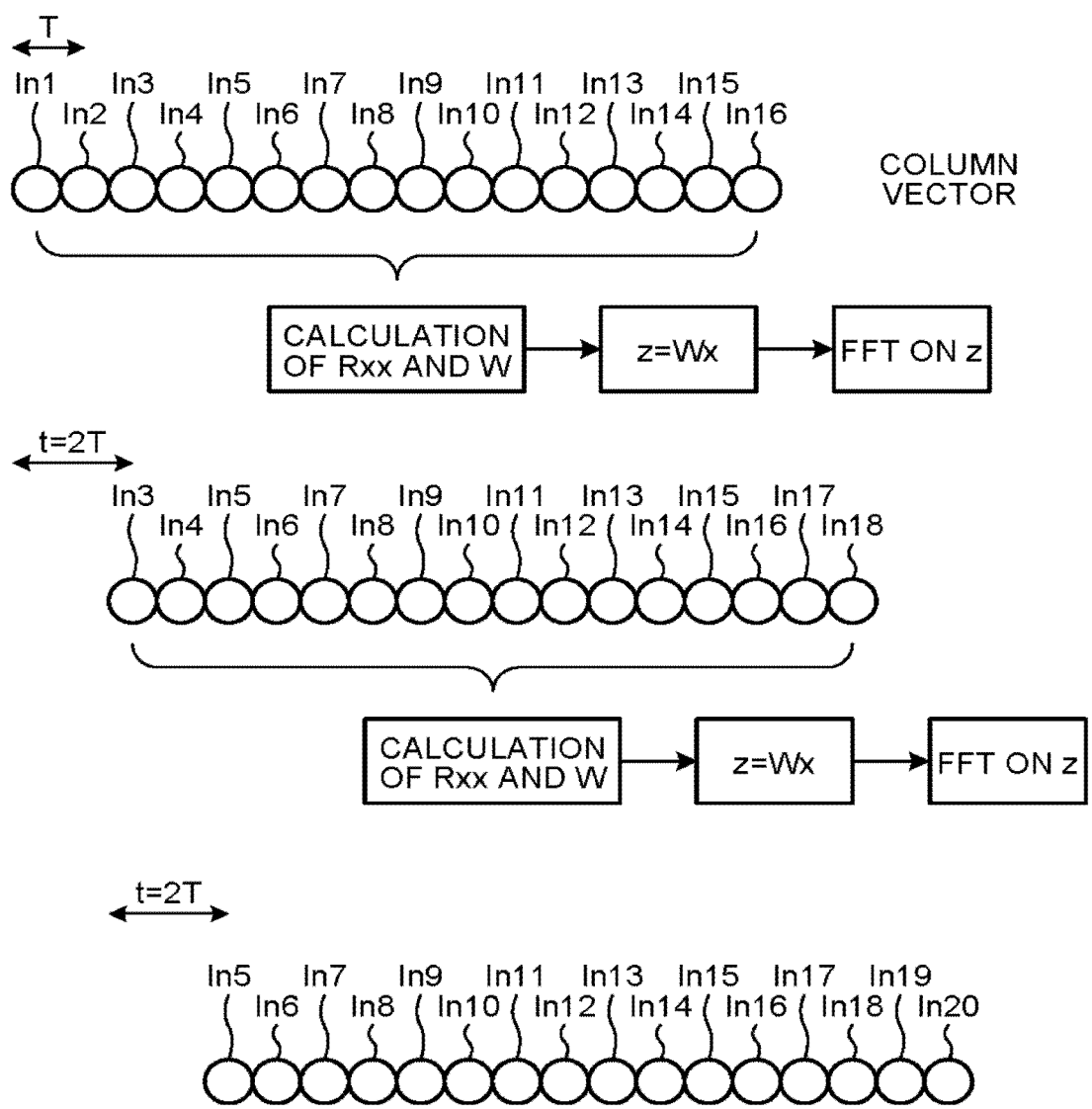
FIG. 15 is a diagram for explaining the second embodiment.

Returning to FIG. 13, the descriptions thereof are continued. The Doppler processing circuitry 14c according to the second embodiment includes correlation matrix calculating circuitry 141a, filter matrix calculating circuitry 142a, MTI filter processing circuitry 143a, and estimating circuitry 144a as illustrated in FIG. 13, and executes both processing for Doppler data generation according to the CFM method and processing for Doppler data generation according to the PWD method. With reference to FIG. 15, descriptions are given of a case where the Doppler processing circuitry 14c according to the second embodiment generates Doppler data using the PWD method. FIG. 15 is a diagram for explaining the second embodiment.

FIG. 15 explains a case where the Doppler processing circuitry 14c according to the second embodiment executes processing pursuant to rules illustrated in FIG. 12C. That is, a case where the length of a time series for calculation of a correlation matrix $R_{xx}$ and the number of FFT points are set equal to each other is explained. Here, T denotes a time interval of the time series; t, a time shift interval in FFT transformation; and M, the length of a data string to be input to the MTI filter processing circuitry 143a. In the second embodiment, T is the same as a frame period. In addition, T<t. For the convenience of explanation, t=aT (a: integer), and FIG. 15 illustrates a case where a=2 and M=16.

Functions of the correlation matrix calculating circuitry 141a according to the second embodiment are the same as those of the correlation matrix calculating circuitry 141 according to the first embodiment. The correlation matrix calculating circuitry 141a according to the second embodiment needs to calculate only one correlation matrix $R_{xx}$ for the entire two-dimensional space. In other words, the correlation matrix calculating circuitry 141a uses, as each of the first data strings, a data string of data based on a continuous echo signal acquired from the same position by repeating a scanning form in which transmission and reception of ultrasound waves are executed one time on each scan line in a scanning range formed of a plurality of scan line. The correlation matrix calculating circuitry 141a according to the second embodiment calculates the correlation matrix $R_{xx}$ at every time interval t=aT. For example, if a=2, the amount of calculation for the correlation matrix is reduced to ½.

Functions of the filter matrix calculating circuitry 142a according to the second embodiment are the same as those of the filter matrix calculating circuitry 142 according to the first embodiment. The filter matrix calculating circuitry 142a according to the second embodiment needs to calculate only one filter matrix "W" for the entire two-dimensional space. In the second embodiment, the MTI filter matrix "W"

needs only to be calculated at every time interval t=aT. If a=2, the amount of processing for this calculation is reduced to ½.

The MTI filter processing circuitry 143a according to the second embodiment receives, for example, input of In1 to In16 as a target data string and performs MTI filter processing thereon, as illustrated in the uppermost part of FIG. 15. The MTI filter processing circuitry 143a then selects all of the elements of a data string obtained by the MTI filter processing, and outputs these elements to the estimating circuitry 144a, as illustrated in the uppermost part of FIG. 15.

After the elapse of a time interval of 2T, the MTI filter processing circuitry 143a receives, for example, input of In3 to In18 as a target data string and performs MTI filter processing thereon, as illustrated in the middle part of FIG. 15. The MTI filter processing circuitry 143a then selects all of the elements of a data string obtained by the MTI filter processing, and outputs these elements to the estimating circuitry 144a, as illustrated in the uppermost part of FIG. 15. Similarly, after the elapse of another time interval of 2T, the MTI filter processing circuitry 143a receives, for example, input of In5 to In20 as a target data string and performs MTI filter processing thereon, as illustrated in the lowermost part of FIG. 15. The MTI filter processing circuitry 143a then selects all of the elements of a data string obtained by the MTI filter processing, and outputs these elements to the estimating circuitry 144a. Thus, in the second embodiment, MTI filter processing needs only to be performed at every time interval t=aT. If a=2, the amount of processing for this calculation is reduced to ½. Furthermore, in the second embodiment, FFT is performed with all of output results from MTI filter processing used therein. This manner is efficient when the value of a is large.

Functions of the estimating circuitry 144a according to the second embodiment are the same as those of the estimating circuitry 144 according to the first embodiment. In the example illustrated in FIG. 15, at every time interval 2T, the estimating circuitry 144a performs FFT using output data output from MTI filter processing.

Figure 16A:
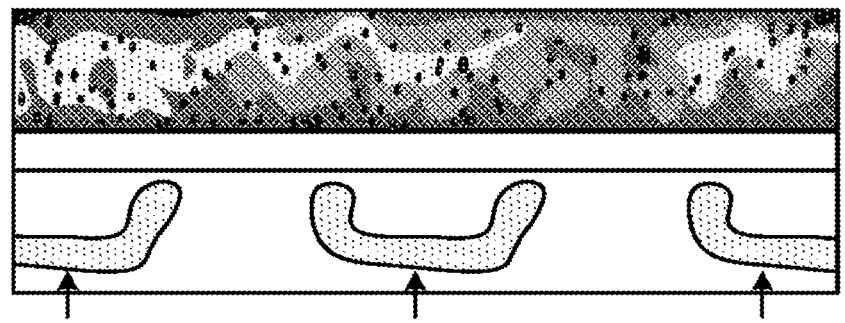
FIG. 16A is a diagram illustrating an example of an FFT waveform obtained without the application of an MTI filter after ultrasound scanning based on the high frame rate method is executed.
Figure 16B:
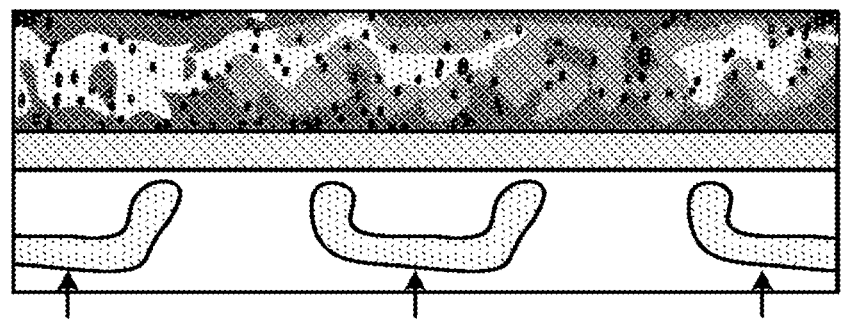
FIG. 16B is a diagram illustrating an example of an FFT waveform obtained with the application of an MTI filter of the IIR type after ultrasound scanning based on the high frame rate method is executed.
Figure 16C:
FIG. 16C is a diagram illustrating an example of an FFT waveform obtained through ultrasound scanning based on the high frame rate method executed by the Doppler processing circuitry according to the second embodiment.

Next, examples of an FFT waveform according to the second embodiment are described with reference to FIG. 16A to FIG. 16C. FIG. 16A to FIG. 16C illustrate cases where a=4 and M=32. FIG. 16A to FIG. 16C illustrate enlarged views of a part of the Doppler waveform 40a illustrated in FIG. 4.

FIG. 16A is a diagram illustrating an example of an FFT waveform obtained without the application of an MTI filter after ultrasound scanning based on the high frame rate method is executed. As illustrated in FIG. 16A, there is a frequency component attributable to clutter visualized. The frequency component attributable to clutter is indicated by the arrows in FIG. 16A.

FIG. 16B is a diagram illustrating an example of an FFT waveform obtained with the application of an MTI filter of the IIR type after ultrasound scanning based on the high frame rate method is executed. In FIG. 16B, there is a frequency component attributable to clutter visualized as in FIG. 16A. The frequency component attributable to clutter is indicated by the arrows in FIG. 16B.

FIG. 16C is a diagram illustrating an example of an FFT waveform obtained through ultrasound scanning based on the high frame rate method executed by the Doppler processing circuitry according to the second embodiment. FIG. 16C indicates that clutter resulting in Doppler frequencies higher than the Doppler frequency of the blood flow was able to be considerably reduced. As illustrated in FIG. 16C, this ultrasound scanning makes it possible to exclusively display blood flow signals even when the Doppler frequency of a blood flow and a frequency component attributable to clutter overlap each other.

Observation of an FFT display image containing only blood flow signals is enabled by elimination of clutter noise mixed into an FFT display image according to the PWD method, which spreads over a wide Doppler frequency range, and clutter noise the Doppler frequency of which is higher than the Doppler frequency of a blood flow. Consequently, a diagnosis of a blood flow can be made on an FFT display image without being distracted by clutter noise.

As described above, the second embodiment enables noise to be reduced on an FFT display according to the PWD method when ultrasound scanning based on the high frame rate method is executed.

In addition, while designation of only one range gate is allowed in the first embodiment, designation of a plurality of range gates at any desired positions in a two-dimensional space within a scanning range is allowed in the case of the ultrasound scanning based on the high frame rate method according to the second embodiment.

The Doppler processing circuitry 14c according to the second embodiment may be configured to execute processing pursuant to rules other than the rules illustrated in FIG. 12C. For example, the MTI filter processing circuitry 143a according to the second embodiment may shift the time-series data on a frame to frame basis and output one element at the center of each output vector. In this case, for example, the correlation matrix calculating circuitry 141a according to the second embodiment calculates a correlation matrix $R_{xx}$ with respect to each frame. The filter matrix calculating circuitry 142a according to the second embodiment calculates an MTI filter matrix "W" with respect to each frame.

When the Doppler processing circuitry 14c according to the second embodiment generates Doppler data using CFM method, the correlation matrix calculating circuitry 141a and the filter matrix calculating circuitry 142a executes the same processing as described for the case using the PWD method. The MTI filter processing circuitry 143a performs a calculation expressed as Mathematical Formula (6) with respect to each sample point. Consequently, the MTI filter processing circuitry 143a outputs output data for each sample point to the estimating circuitry 144a. Based on the extracted data strings of signals from a moving body, the estimating circuitry 144a estimates moving body information on the moving body. For example, the estimating circuitry 144a estimates blood flow information at a position "m" by performing autocorrelation calculation processing and estimation processing of the velocity, the dispersion, and the power from column vectors "$y_m$", which are output data for a position "m".

Other Embodiments

Embodiments are not limited to the embodiments described below.

In the PWD method in which ultrasound waves are transmitted a plurality of times and echo signals are received a plurality of times as in conventional cases, FFT waveforms from only one point at which a range gate is set. In recent years, the use of a technique for transmitting plane waves to acquire all of the reception rasters from transmission performed one time has enabled FFT waveforms to be displayed with range gates set at any desired plurality of points in a two-dimensional image. The first and the second embodiments and the modifications described above are applicable to such a case.

The components of the apparatuses and devices illustrated in the drawings in connection with descriptions of the above embodiments are functionally conceptual, and do not necessarily need to be physically configured as illustrated. That is, specific forms of distribution and integration of the devices are not limited to those illustrated in the drawings. All or part thereof may be functionally or physically distributed/integrated in any desired units depending on various loads or usage states. For example, the correlation matrix calculating circuitry 141 and the filter matrix calculating circuitry 142 may be integrated into filter coefficient acquiring circuitry. In this case, for example, based on a result of a principal component analysis using first data strings that are sets of data generated based on echo signals caused by transmission of ultrasound waves on the same scan line, the filter coefficient acquiring circuitry obtains a filter coefficient that suppresses clutter components. The MTI filter processing circuitry 143 and the estimating circuitry 144 may also be integrated into deriving circuitry. In this case, for example, the deriving circuitry uses the filter coefficient to: obtain, from target data strings contained in a region of interest among the first data strings, a second data string that is a set of data derived from echo signals based on a moving body present in the region of interest; and then derive waveform information by performing a frequency analysis on the second data string. The image generating circuitry 15 and the processing circuitry 17 may be integrated into control circuitry. In this case, for example, the control circuitry generates a waveform information image based on the wave information and causes the monitor 2 to display the waveform information image.

All or some of processing functions executed by the devices may be implemented by a central processing unit (CPU) and a computer program analyzed and executed by the CPU, or implemented as hardware using wired logic.

The control method described in the above embodiments can be performed by executing a control program prepared in advance on a computer such as a personal computer or a workstation. The control program can be distributed via a network such as the Internet. The control program can be recorded in a computer-readable recording medium such as a hard disk, a flexible disk (FD), a compact disc read only memory (CD-ROM), a magneto optical disk (MO), or a digital versatile disc (DVD), and can be read by the computer from the recording medium to be executed.

Image Processing Apparatus

The above descriptions relate to cases where each of the image processing methods described in the first and the second embodiments and the modifications is executed in an ultrasound diagnosis apparatus. However, each of the image processing methods described in the first and the second embodiments and the modifications may be executed in an image processing apparatus capable of acquiring signals received by the ultrasound probe 1. Such an image processing apparatus can generate an FFT waveform with a range gate set at any desired position. For example, even after a patient has gone after the completion of a real-time examination using an ultrasound diagnosis apparatus, data can be read out, so that an FFT waveform is generated with a range gate set at any desired position. In this manner, an FFT waveform can be generated at a position that is different from a position are which an FFT waveform has been generated in a real-time examination. The image processing apparatus may generate FFT waveforms with range gates set at a plurality of positions.

According to at least one of the embodiments described above, noise can be reduced in an FFT display according to the PWD method.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasound diagnosis apparatus for performing a Pulse Wave Doppler (PWD) method, the apparatus comprising:

calculating circuitry configured to generate an averaged data string by averaging first data strings which are obtained for different positions on a scan line on which a range gate is set, and calculate a correlation matrix based on the averaged data string;

filter coefficient acquiring circuitry configured to, based on a result of a principal component analysis using the correlation matrix, obtain a filter matrix including a filter coefficient that suppresses clutter components;

deriving circuitry configured to
obtain a target data string by adding the first data strings which are obtained for the different positions on the scan line on which the range gate is set,
obtain a filtered data string by filtering the target data string using the filter matrix,
select only a part of the filtered data string,
store the selected part of the filtered data string in a memory,
determine whether a suitable amount of data to perform a Fast Fourier Transform (FFT) has been accumulated in the memory, and
derive waveform information indicating temporal changes of a moving body in the range gate, by performing the FFT on a second data string consisting of the stored data when it is determined that the suitable amount of data has been accumulated in the memory; and control circuitry configured to generate a waveform information image based on the waveform information and cause a monitor to display the waveform information image, wherein the deriving circuitry is configured to determine a number of principal components to be suppressed in the principal component analysis based on a threshold that is changed in accordance with a magnitude of an eigenvalue of the correlation matrix.

2. The ultrasound diagnosis apparatus according to claim 1, wherein the filter coefficient acquiring circuitry is further configured to use, as each of the first data strings, a data string of data based on a continuous echo signal acquired from a same position by repeating a scanning form in which transmission and reception of ultrasound waves are executed one time on each scan line in a scanning range formed of a plurality of scan lines.

3. The ultrasound diagnosis apparatus according to claim 2, wherein the filter coefficient acquiring circuitry is further configured to use, as each of the first data strings, a data string on a scan line on which a region of interest has been set.

4. The ultrasound diagnosis apparatus according to claim 3, wherein the deriving circuitry is further configured to
set, as pieces of data that form the second data string, a certain number of pieces of data that form output data strings obtained by processing the target data strings with the filter coefficient, and
when the pieces of data that form the second data string have accumulated to correspond to a number of FFT points, perform the FFT on the second data string to derive the waveform information.

5. The ultrasound diagnosis apparatus according to claim 2, wherein the filter coefficient acquiring circuitry is further configured to use, as the first data strings, data strings on a plurality of scan lines including at least a scan line on which a region of interest has been set.

6. The ultrasound diagnosis apparatus according to claim 5, wherein the deriving circuitry is further configured to
set, as pieces of data that form the second data string, a certain number of pieces of data that form output data strings obtained by processing the target data strings with the filter coefficient, and
when the pieces of data that form the second data string have accumulated to correspond to a number of FFT points, perform the FFT on the second data string to derive the waveform information.

7. The ultrasound diagnosis apparatus according to claim 2, wherein the deriving circuitry is further configured to
set, as pieces of data that form the second data string, a certain number of pieces of data that form output data strings obtained by processing the target data strings with the filter coefficient, and
when the pieces of data that form the second data string have accumulated to correspond to a number of FFT points, perform the FFT on the second data string to derive the waveform information.

8. The ultrasound diagnosis apparatus according to claim 1, wherein the filter coefficient acquiring circuitry is further configured to use, as each of the first data strings, a data string on a scan line on which a region of interest has been set.

9. The ultrasound diagnosis apparatus according to claim 8, wherein the deriving circuitry is further configured to
set, as pieces of data that form the second data string, a certain number of pieces of data that form output data strings obtained by processing the target data strings with the filter coefficient, and
when the pieces of data that form the second data string have accumulated to correspond to a number of FFT points, perform the FFT on the second data string to derive the waveform information.

10. The ultrasound diagnosis apparatus according to claim 1, wherein the filter coefficient acquiring circuitry is further configured to use, as the first data strings, data strings on a plurality of scan lines including at least a scan line on which a region of interest has been set.

11. The ultrasound diagnosis apparatus according to claim 10, wherein the deriving circuitry is further configured to
set, as pieces of data that form the second data string, a certain number of pieces of data that form output data strings obtained by processing the target data strings with the filter coefficient, and
when the pieces of data that form the second data string have accumulated to correspond to a number of FFT points, perform the FFT on the second data string to derive the waveform information.

12. The ultrasound diagnosis apparatus according to claim 1, wherein the deriving circuitry is further configured to
set, as pieces of data that form the second data string, a certain number of pieces of data that form output data strings obtained by processing the target data strings with the filter coefficient, and
when the pieces of data that form the second data string have accumulated to correspond to a number of FFT points, perform the FFT on the second data string to derive the waveform information.

13. The ultrasound diagnosis apparatus according to claim 1, wherein a data length of each of the target data strings and a number of pieces of data that are redundant in adjacent pieces of data in the target data strings are previously determined.

14. An image processing apparatus for performing a Pulse Wave Doppler (PWD) method, the method comprising:
calculating circuitry configured to generate an averaged data string by averaging first data strings which are obtained for different positions on a scan line on which a range gate is set, and calculate a correlation matrix based on the averaged data string;
filter coefficient acquiring circuitry configured to, based on a result of a principal component analysis using the correlation matrix, obtain a filter matrix including a filter coefficient that suppresses clutter components;
deriving circuitry configured to
obtain a target data string by adding the first data strings which are obtained for the different positions on the scan line on which the range gate is set,
obtain a filtered data string by filtering the target data string using the filter matrix,
select only a part of the filtered data string,
store the selected part of the filtered data string in a memory,
determine whether a suitable amount of data to perform a Fast Fourier Transform (FFT) has been accumulated in the memory, and
derive waveform information indicating temporal changes of a moving body in the range gate, by performing the FFT on a second data string consisting of the stored data when it is determined that the suitable amount of data has been accumulated in the memory; and
control circuitry configured to generate a waveform information image based on the waveform information and cause a monitor to display the waveform information image,
wherein the deriving circuitry is configured to determine a number of principal components to be suppressed in the principal component analysis based on a threshold that is changed in accordance with a magnitude of an eigenvalue of the correlation matrix.

* * * * *